(12) United States Patent
Sabelle et al.

(10) Patent No.: US 7,384,432 B2
(45) Date of Patent: Jun. 10, 2008

(54) SECONDARY PARA-PHENYLENEDIAMINES HAVING A CARBOXYL GROUP, DYE COMPOSITIONS COMPRISING THE SAME, AND DYEING PROCESSES USING THE COMPOSITIONS

(75) Inventors: Stéphane Sabelle, Paris (FR); Eric Metais, St-leu-le-Foret (FR); Philippe Breton, Noisy le Roi (FR)

(73) Assignee: L'Oreal S.A., Paris (FR)

( * ) Notice: Subject to any disclaimer, the term of this patent is extended or adjusted under 35 U.S.C. 154(b) by 81 days.

(21) Appl. No.: 11/066,450

(22) Filed: Feb. 28, 2005

(65) Prior Publication Data

US 2006/0021159 A1   Feb. 2, 2006

Related U.S. Application Data

(60) Provisional application No. 60/568,265, filed on May 6, 2004.

(30) Foreign Application Priority Data

Feb. 27, 2004   (FR) .................................. 0402026

(51) Int. Cl.
    *A61K 7/13* (2006.01)
(52) U.S. Cl. .................. 8/405; 8/406; 8/408; 8/410; 8/411; 8/412; 8/415; 564/307
(58) Field of Classification Search ................ 8/405, 8/406, 408, 410, 411, 412, 415; 564/307
See application file for complete search history.

(56) References Cited

U.S. PATENT DOCUMENTS

| RE30,199 E | 1/1980 | Rose et al. |
|---|---|---|
| 4,823,985 A | 4/1989 | Grollier et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Mockli |
| 5,766,576 A | 6/1998 | Lowe et al. |
| 6,099,592 A | 8/2000 | Vidal et al. |
| 6,099,593 A | 8/2000 | Terranova et al. |
| 6,284,003 B1 | 9/2001 | Rose et al. |
| 6,338,741 B1 | 1/2002 | Vidal et al. |
| 6,630,004 B1* | 10/2003 | Philippe et al. ............... 8/409 |
| 6,645,258 B2 | 11/2003 | Vidal et al. |
| 6,730,789 B1 | 5/2004 | Birault et al. |

FOREIGN PATENT DOCUMENTS

| DE | 23 59 399 A1 | 6/1975 |
|---|---|---|
| DE | 38 43 892 A1 | 6/1990 |
| DE | 41 33 957 A1 | 4/1993 |
| DE | 195 43 988 A1 | 5/1997 |
| EP | 0 714 954 | 6/1996 |
| EP | 0 770 375 A1 | 5/1997 |
| EP | 0 908 445 | 4/1999 |
| FR | 1 141 548 | 9/1957 |
| FR | 1141548 * | 9/1957 |
| FR | 2 586 913 A1 | 3/1987 |
| FR | 2 733 749 A1 | 11/1996 |
| FR | 2 801 308 A1 | 5/2001 |
| GB | 1 026 978 A | 4/1966 |
| GB | 1 153 196 A | 5/1969 |
| JP | 02-19576 A | 1/1990 |
| JP | 05-163124 A | 6/1993 |
| JP | 2526099 B2 | 8/1996 |
| WO | WO 94/08969 A1 | 4/1994 |
| WO | WO 94/08970 A1 | 4/1994 |
| WO | WO 95/01772 | 1/1995 |
| WO | WO 95/15144 | 6/1995 |
| WO | WO 96/15765 A1 | 5/1996 |

OTHER PUBLICATIONS

XP 002298524, XP 002298525 and XP 002298526.*
STIC Search Report dated Feb. 7, 2007.*
Chemical Abstracts, Columbus, OH, US; Accession No. 1986:608809, XP002298526, for Divakar et al., "Quinone imine route to benzimidazol-2-ylcarbamates. Part 3. Effect of extension of conjugation in the quinone imine," J. of Chem. Research (1986), (5), p. 161.
Chemical Abstracts, Columbus, OH, US; Accession No. 1991:647455, XP002298525, for Patel et al., "Novel inhibitors of enkephalin-degrading enzymes. III: 4-Carboxymethylamino-4-oxo-3-(phenylamino)butanoic acids as enkephalinase inhibitors," J. of Enzyme Inhibition (1991), 5(2), pp. 133-149.
Chemical Abstracts, Columbus, OH, US; Accession No. 1998:374037, XP002298524, for Okey et al., "Predicting stability constants of various chelating agents using QSAR technology," Emerging Technologies in Hazardous Waste Management 7, (1996), pp. 49-68.

(Continued)

*Primary Examiner*—Eisa Elhilo
(74) *Attorney, Agent, or Firm*—Finnegan, Henderson, Farabow, Garrett, & Dunner, L.L.P.

(57) ABSTRACT

The present disclosure relates to novel secondary para-phenylenediamines having a carboxyl group. The present disclosure further relates to a dye composition comprising at least one secondary para-phenylenediamine for dyeing keratin fibers, such as human hair, a process for preparing the composition, and a process and kit for dyeing keratin fibers using the composition.

30 Claims, No Drawings

OTHER PUBLICATIONS

Jani et al., "Synthesis of some aminoacetamide derivatives," J. Indian. Chem. Soc., (1990), 67, pp. 602-603.

Kotsuki et al., "High pressure organic chemistry; XII. A convenient synthesis of aromatic amines from activated aromatic fluorides," Synthesis, (1990), (12), pp. 1147-1148.

Massa et al., "Spiro-[4H-pyrrolo[1,2-a][1,4]benzodiazepine-4,4'-piperidine derivatives as potential nootropic agents: A simple one-pot synthesis," Synth. Commun., (1990), 20(22), pp. 3537-3545.

Orelli et al., "Selective monoformylation of 1,3-diaminopropane derivates," Synth. Commun., (1999), 29(11), pp. 1819-1833.

English language Derwent Abstract of EP 0 770 375 A1, (1997).

English language Derwent Abstract of JP 02-19576 A, (1990).

English language Derwent Abstract of JP 05-163124 A, (1993).

English language Derwent Abstract of JP 2526099 B2, (1996).

French Search Report for FR 04 02026 (Priority Application for U.S. Application No. 11/066,450), dated Sep. 30, 2004.

\* cited by examiner

SECONDARY PARA-PHENYLENEDIAMINES HAVING A CARBOXYL GROUP, DYE COMPOSITIONS COMPRISING THE SAME, AND DYEING PROCESSES USING THE COMPOSITIONS

CROSS-REFERENCE TO RELATED APPLICATION

This application claims benefit of U.S. Provisional Application No. 60/568,265, filed May 6, 2004, which is incorporated herein by reference.

FIELD OF THE INVENTION

The present disclosure relates to a novel family of secondary para-phenylenediamines having a carboxyl group, to compositions comprising secondary para-phenylenediamines having a carboxyl group, to the preparation of the compounds and compositions and to their use for the oxidation dyeing of keratin fibers.

BACKGROUND OF THE INVENTION

It is known practice to dye keratin fibers, such as human hair, with dye compositions containing oxidation dye precursors, such as ortho- or para-phenylenediamines, ortho- or para-aminophenols, and heterocyclic compounds, which are generally referred to as oxidation bases. These oxidation bases can be colorless or weakly colored compounds which, when combined with oxidizing products, may give rise to colored compounds by a process of oxidative condensation.

It is also known that the shades obtained with these oxidation bases may be varied by combining them with couplers or coloration modifiers, which may be chosen from aromatic meta-diaminobenzenes, meta-aminophenols, meta-diphenols and certain heterocyclic compounds such as indole compounds.

The variety of molecules that can be used as oxidation bases and couplers makes it possible to obtain a wide range of colors.

The "permanent" coloration obtained by means of these oxidation dyes should, moreover, satisfy a certain number of requirements. Thus, it should not have toxicological drawbacks, it may allow shades of the desired intensity to be obtained, and it may have good resistance to external agents such as light, bad weather, washing, permanent waving, perspiration and rubbing.

The dyes may also allow white hairs to be covered, and lastly, they may be as unselective as possible, i.e., they may allow the smallest possible differences in coloration to be produced over the entire length of the same keratin fiber, which is generally differently sensitized (e.g., damaged) between its end and its root.

SUMMARY OF THE INVENTION

The present inventor has discovered, surprisingly and advantageously, that it is possible to obtain a novel family of secondary para-phenylenediamines having a carboxyl group, capable of giving strong, aesthetic and sparingly selective colorations in varied shades, which show good resistance to the various attacking factors to which the fibers may be subjected. The present disclosure also relates to a process for preparing these secondary para-phenylenediamines having a carboxyl group, and also to their use in the oxidation dyeing of the hair.

Another aspect of the present disclosure relates to compositions for dyeing keratin fibers, such as human keratin fibers including hair, comprising at least one secondary para-phenylenediamine having a carboxyl group, which may allow the production of colorations having the advantages mentioned above. In addition, these compositions have a good toxicological profile.

Another aspect of the present disclosure is a dyeing process using this composition for dyeing keratin fibers, such as human keratin fibers including hair, and a multi-compartment device or dyeing "kit".

The composition as disclosed herein can make it possible to obtain very strong, sparingly selective coloration of the keratin fibers that is resistant with respect to external agents, such as light, while avoiding the degradation of these fibers.

Other aspects and benefits of the present disclosure will emerge even more clearly upon reading the description and the non-limiting examples that follow.

DETAILED DESCRIPTION OF THE INVENTION

The novel secondary para-phenylenediamines according to the present disclosure are compounds of formula (I) and the addition salts thereof:

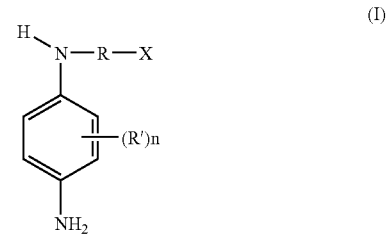

wherein:
n is an integer ranging from 0 to 4,
if n ranges from 1 to 4, then R is a linear or branched $C_2$-$C_{10}$ alkylene radical, which is unsubstituted or substituted with at least one group chosen from hydroxyl, ($C_1$-$C_{15}$)alkylcarbonyl, carboxyl, amido, ($C_1$-$C_{15}$)alkoxycarbonyl, mono($C_1$-$C_{15}$)alkylaminocarbonyl, and di($C_1$-$C_{15}$)alkylaminocarbonyl radicals, wherein the alkylene radical optionally comprises at least one hetero atom chosen from oxygen and nitrogen;
with the exception of 2-N-(3-methoxy-4-aminophenyl)aminoethanoic acid;
if n is equal to 0, then R is a linear or branched $C_2$-$C_{10}$ alkylene radical, which is unsubstituted or substituted with at least one group chosen from hydroxyl, $C_1$-$C_{15}$ alkoxy, ($C_1$-$C_{15}$)alkylcarbonyl, carboxyl, amido, ($C_1$-$C_{15}$)alkoxycarbonyl, and mono- or di($C_1$-$C_{15}$)alkylaminocarbonyl radicals, wherein the alkylene radical optionally comprises at least one hetero atom chosen from oxygen and nitrogen;
with the exception of
6-N-(4-aminophenyl)aminocaproic acid,
3-N-(4-aminophenyl)aminopropanoic acid, and
4-N-(4-aminophenyl)aminobutanoic acid;
X is a radical —COOY, wherein Y is chosen from:
a hydrogen atom;
a $C_1$-$C_{15}$ alkyl radical; and
a $C_1$-$C_{15}$ monohydroxyalkyl or polyhydroxyalkyl radical;

R' is chosen from a $C_1$-$C_{15}$ alkyl radical, a $C_1$-$C_{15}$ alkoxy radical, a $C_1$-$C_{15}$ hydroxyalkoxy radical, a ($C_1$-$C_{15}$) alkoxy($C_1$-$C_{15}$)alkyl radical, a $C_1$-$C_{15}$ monohydroxyalkyl radical, and a $C_1$-$C_{15}$ polyhydroxyalkyl radical, and a chlorine atom.

For example, in one embodiment of the composition as disclosed herein, when n is equal to 0, then the group R of formula (I) can be a linear or branched $C_2$-$C_{10}$ alkylene radical, such as ethylene, propylene, butylene, pentylene or hexylene, which is unsubstituted or substituted with at least one group chosen from ($C_2$-$C_8$)alkylcarbonyl, carboxyl and ($C_2$-$C_8$)alkoxycarbonyl, wherein the alkylene radical optionally comprises at least one oxygen atom.

In another embodiment of the present disclosure, when n ranges from 1 to 4, then the group R of formula (I) can be a linear or branched $C_2$-$C_{10}$ alkylene radical, such as ethylene, propylene, butylene, pentylene or hexylene, which can be unsubstituted or substituted with at least one group chosen from ($C_2$-$C_8$)alkylcarbonyl, carboxyl and ($C_2$-$C_8$) alkoxycarbonyl, wherein the alkylene radical optionally comprises at least one oxygen atom.

In one embodiment of the present disclosure, the group X of formula (I) is a radical —COOY, wherein Y is chosen from a hydrogen atom and a $C_1$-$C_6$ alkyl radical, such as methyl, ethyl, isopropyl or tert-butyl.

In another non-limiting example, the group R' of formula (I) is chosen from a $C_1$-$C_6$ alkyl radical, such as methyl, ethyl, n-propyl, or isopropyl, a $C_1$-$C_6$ alkoxy radical, a $C_1$-$C_6$ hydroxyalkoxy radical, such as β-hydroxyethoxy, a ($C_1$-$C_6$)alkoxy($C_1$-$C_6$)alkyl radical, and a $C_1$-$C_6$ monohydroxyalkyl or polyhydroxyalkyl radical.

Mention may be made of the following non-limiting examples of compounds of formula (I), chosen from:

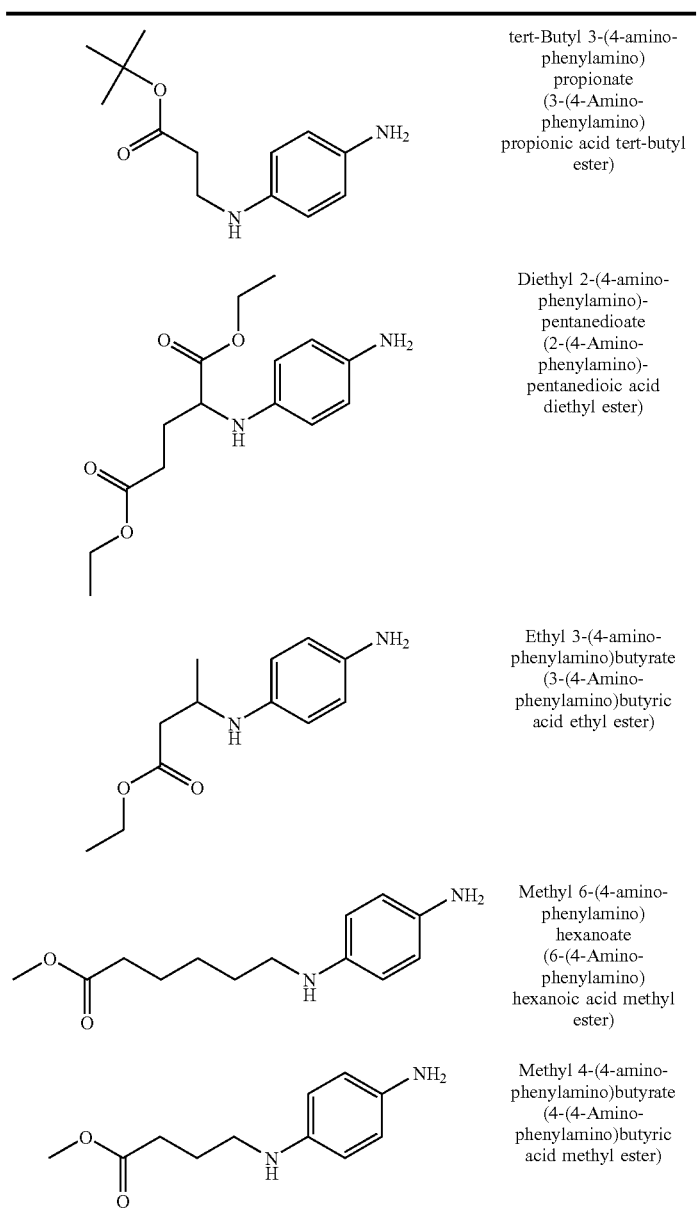

tert-Butyl 3-(4-aminophenylamino)propionate (3-(4-Aminophenylamino) propionic acid tert-butyl ester)

Diethyl 2-(4-aminophenylamino)-pentanedioate (2-(4-Aminophenylamino)-pentanedioic acid diethyl ester)

Ethyl 3-(4-aminophenylamino)butyrate (3-(4-Aminophenylamino)butyric acid ethyl ester)

Methyl 6-(4-aminophenylamino)hexanoate (6-(4-Aminophenylamino) hexanoic acid methyl ester)

Methyl 4-(4-aminophenylamino)butyrate (4-(4-Aminophenylamino)butyric acid methyl ester)

-continued

| | |
|---|---|
| 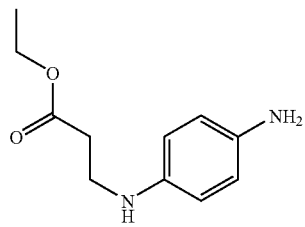 | Ethyl 3-(4-amino-phenylamino)propionate (3-(4-Aminophenyl-amino)propionic acid ethyl ester) |
| 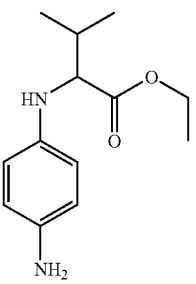 | Ethyl 2-(4-amino-phenylamino)-3-methyl-butyrate (2-(4-Amino-phenylamino)-3-methyl-butyric acid ethyl ester) |
| 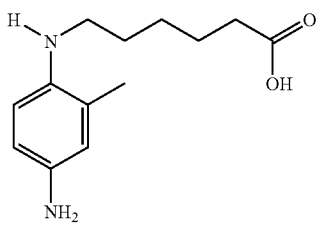 | 6-(4-Amino-2-methyl-phenylamino)hexanoic acid (6-(4-Amino-2-methyl-phenylamino)hexanoic acid) |
| 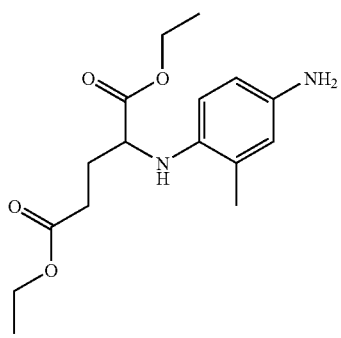 | Diethyl 2-(4-amino-2-methylphenylamino)-pentanedioate (2-(4-Amino-2-methyl-phenylamino)-pentanedioic acid diethyl ester) |
| 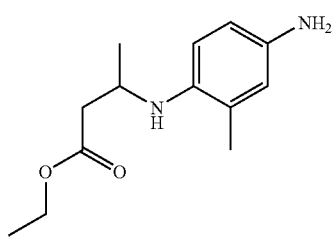 | Ethyl 3-(4-amino-2-methylphenylamino)-butyrate (3-(4-Amino-2-methyl-phenylamino)butyric acid ethyl ester) |
| 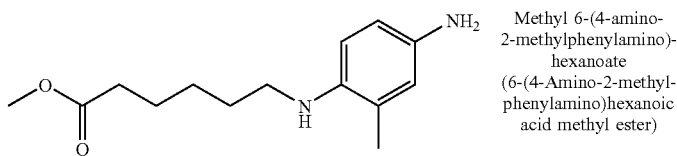 | Methyl 6-(4-amino-2-methylphenylamino)-hexanoate (6-(4-Amino-2-methyl-phenylamino)hexanoic acid methyl ester) |

-continued

| Structure | Name |
|---|---|
| 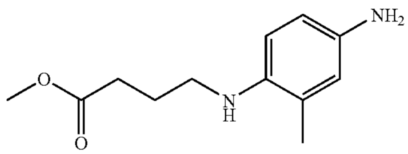 | Methyl 4-(4-amino-2-methylphenylamino)-butyrate (4-(4-Amino-2-methyl-phenylamino)butyric acid methyl ester) |
| 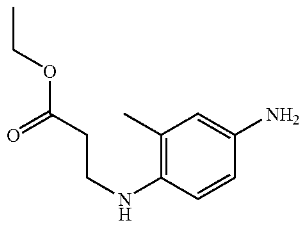 | Ethyl 3-(4-amino-2-methylphenylamino)-propionate (3-(4-Amino-2-methyl-phenylamino) propionic acid ethyl ester) |
| 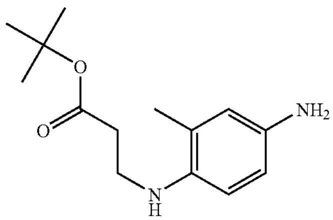 | tert-Butyl 3-(4-amino-2-methylphenylamino)-propionate (3-(4-Amino-2-methyl-phenylamino) propionic acid tert-butyl ester) |
| 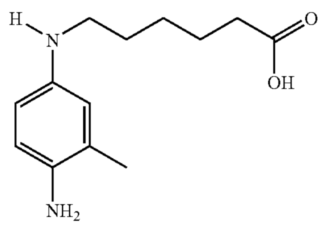 | 6-(4-Amino-3-methyl-phenylamino) hexanoic acid (6-(4-Amino-3-methyl-phenylamino) hexanoic acid) |
| 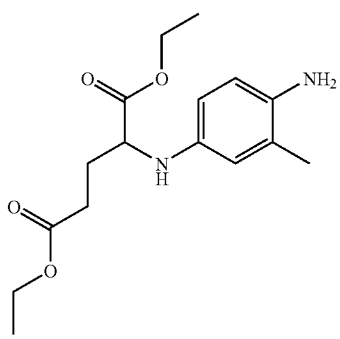 | Diethyl 2-(4-amino-3-methylphenylamino)-pentanedioate (2-(4-Amino-3-methyl-phenylamino)-pentanedioic acid diethyl ester) |
| 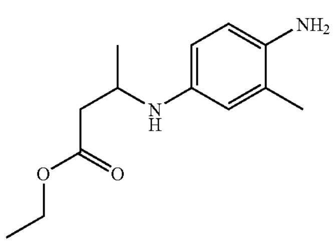 | Ethyl 3-(4-amino-3-methylphenylamino)-butyrate (3-(4-Amino-3-methyl-phenylamino)butyric acid ethyl ester) |
| 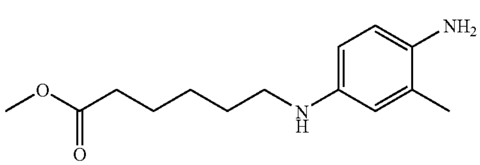 | Methyl 6-(4-amino-3-methylphenylamino)-hexanoate (6-(4-Amino-3-methyl-phenylamino) hexanoic acid methyl ester) |

-continued

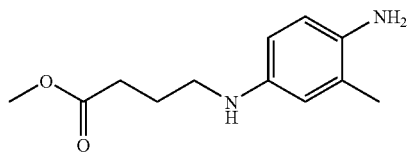

Methyl 4-(4-amino-3-methylphenylamino)-butyrate
(4-(4-Amino-3-methyl-phenylamino)butyric acid methyl ester)

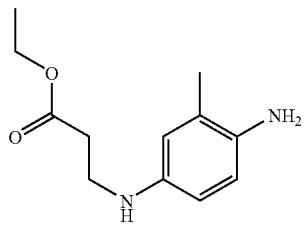

Ethyl 3-(4-amino-3-methylphenylamino)-propionate
(3-(4-Amino-3-methyl-phenylamino) propionic acid ethyl ester)

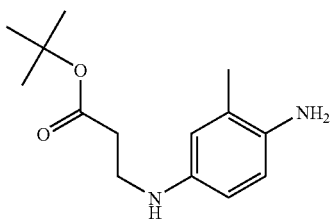

tert-Butyl 3-(4-amino-3-methylphenylamino)-propionate
(3-(4-Amino-3-methyl-phenylamino) propionic acid tert-butyl ester)

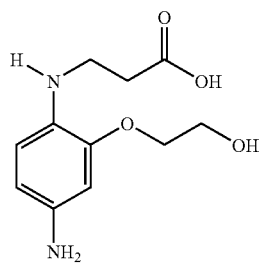

3-[4-Amino-2-(2-hydroxyethoxy)-phenylamino] propionic acid
(3-[4-Amino-2-(2-hydroxyethoxy)-phenylamino] propionic acid)

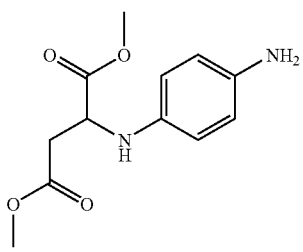

Dimethyl 2-(4-amino-phenylamino) succinate
(2-(4-Amino-phenylamino) succinic acid dimethyl ester)

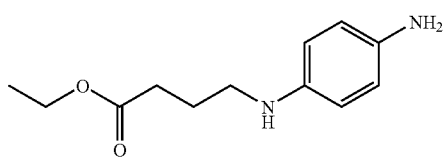

Ethyl 4-(4-amino-phenylamino) butyrate
(4-(4-Amino-phenylamino)butyric acid ethyl ester)

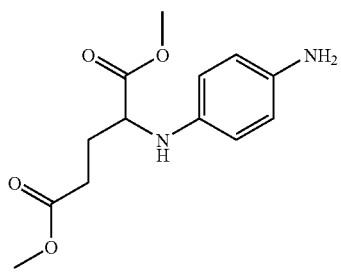

Dimethyl 2-(4-amino-phenylamino)-pentanedioate
(2-(4-Amino-phenylamino)-pentanedioic acid dimethyl ester)

-continued

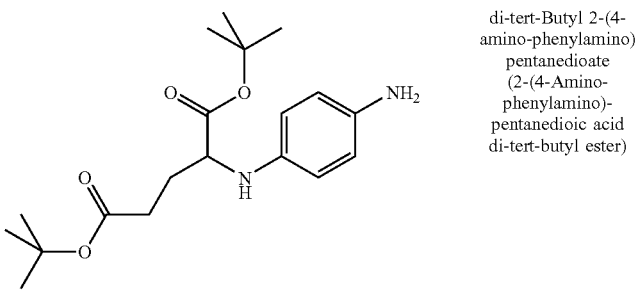

di-tert-Butyl 2-(4-amino-phenylamino)pentanedioate (2-(4-Amino-phenylamino)-pentanedioic acid di-tert-butyl ester)

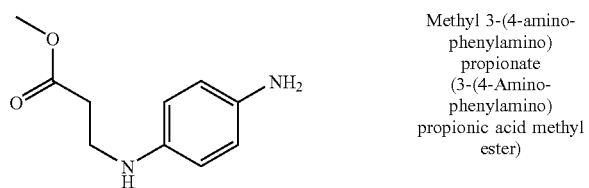

Methyl 3-(4-amino-phenylamino)propionate (3-(4-Amino-phenylamino)propionic acid methyl ester)

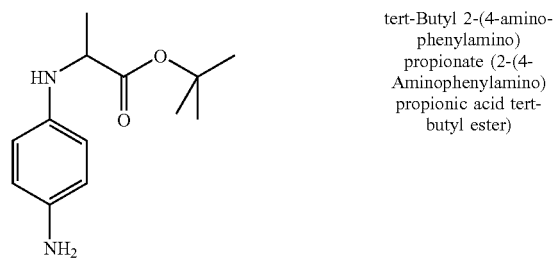

tert-Butyl 2-(4-amino-phenylamino)propionate (2-(4-Aminophenylamino)propionic acid tert-butyl ester)

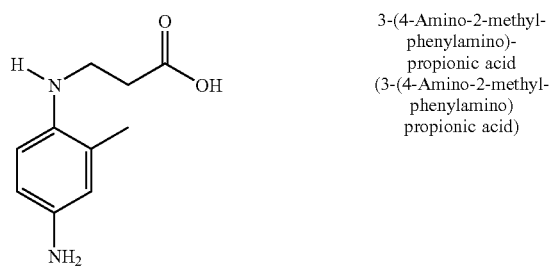

3-(4-Amino-2-methyl-phenylamino)-propionic acid (3-(4-Amino-2-methyl-phenylamino)propionic acid)

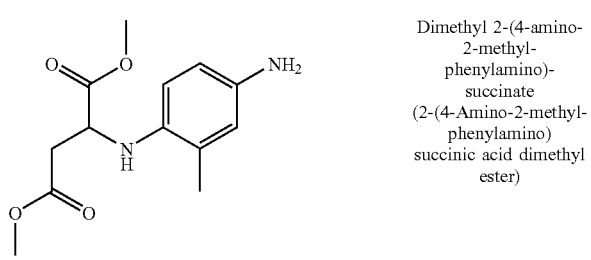

Dimethyl 2-(4-amino-2-methyl-phenylamino)-succinate (2-(4-Amino-2-methyl-phenylamino)succinic acid dimethyl ester)

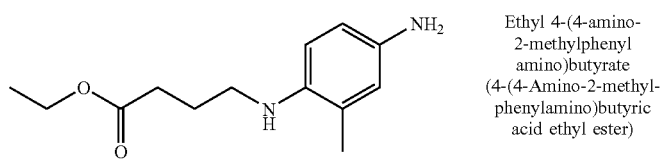

Ethyl 4-(4-amino-2-methylphenylamino)butyrate (4-(4-Amino-2-methyl-phenylamino)butyric acid ethyl ester)

-continued

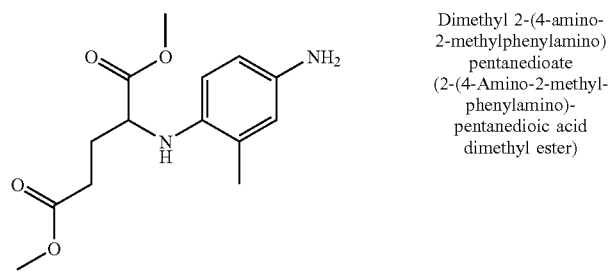

Dimethyl 2-(4-amino-2-methylphenylamino)pentanedioate
(2-(4-Amino-2-methyl-phenylamino)-pentanedioic acid dimethyl ester)

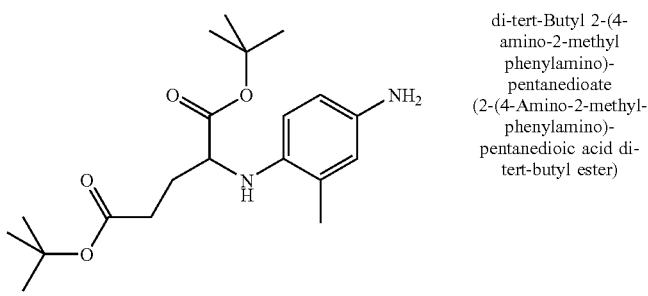

di-tert-Butyl 2-(4-amino-2-methyl phenylamino)-pentanedioate
(2-(4-Amino-2-methyl-phenylamino)-pentanedioic acid di-tert-butyl ester)

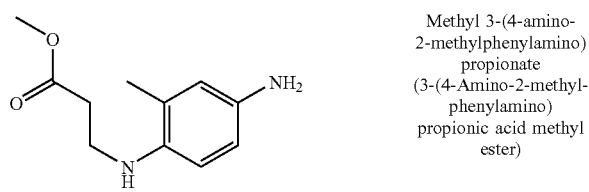

Methyl 3-(4-amino-2-methylphenylamino)propionate
(3-(4-Amino-2-methyl-phenylamino)propionic acid methyl ester)

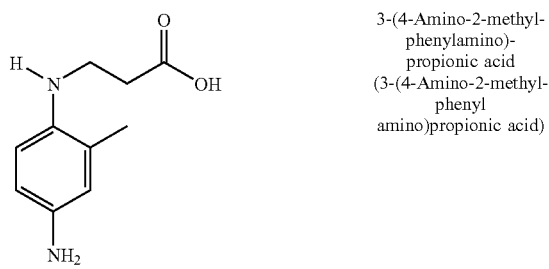

3-(4-Amino-2-methyl-phenylamino)-propionic acid
(3-(4-Amino-2-methyl-phenyl amino)propionic acid)

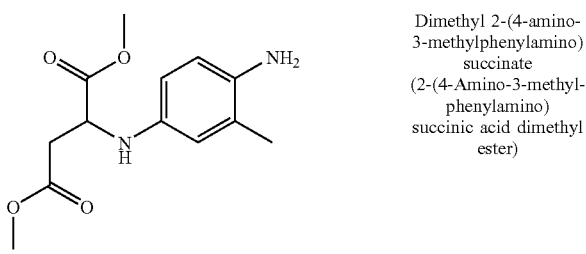

Dimethyl 2-(4-amino-3-methylphenylamino)succinate
(2-(4-Amino-3-methyl-phenylamino)succinic acid dimethyl ester)

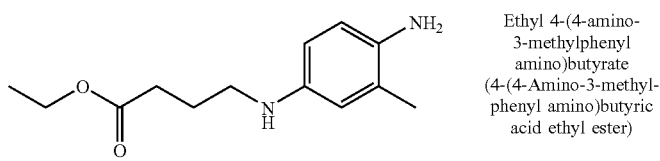

Ethyl 4-(4-amino-3-methylphenyl amino)butyrate
(4-(4-Amino-3-methyl-phenyl amino)butyric acid ethyl ester)

-continued

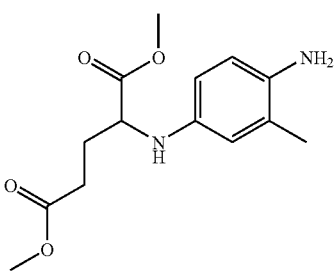

Dimethyl 2-(4-amino-3-methy lphenylamino)-pentanedioate (2-(4-Amino-3-methyl-phenylamino)-pentanedioic acid dimethyl ester)

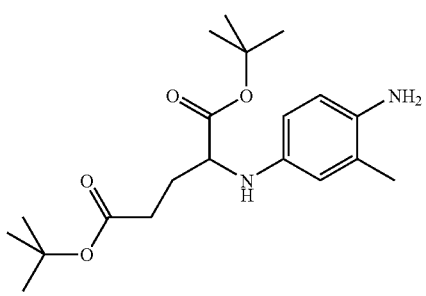

di-tert-Butyl 2-(4-amino-3-methylphenylamino)-pentanedioate (2-(4-Amino-3-methyl-phenylamino)-pentanedioic acid di-tert-butyl ester)

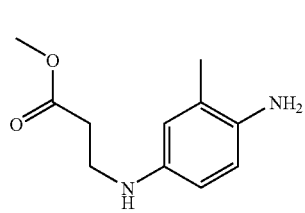

Methyl 3-(4-amino-3-methylphenylamino)-propionate (3-(4-Amino-3-methyl-phenylamino)propionic acid methyl ester)

In one embodiment of the present disclosure, the addition salts may be chosen from the addition salts with an acid, such as the hydrochlorides, hydrobromides, sulfates, citrates, succinates, tartrates, lactates, tosylates, benzenesulfonates, phosphates and acetates.

In one embodiment, the compounds of formula (I) according to the present disclosure may be prepared according to a method that comprises:

nucleophilic substitution of the halogen of the para-halonitrobenzene derivative, with a primary amine of formula X—RNH$_2$ in the presence of a base, R and X being defined as above;

reduction of the nitro function of the compound obtained in the previous step to an amine function, to give the compound of formula (I).

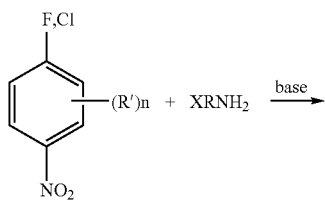

-continued

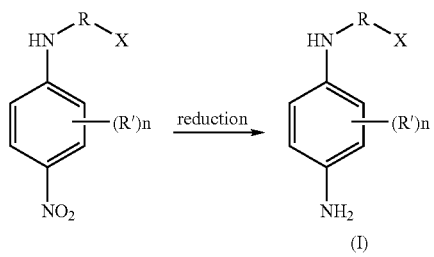

The first synthesis step is described in the scientific reviews Synthesis, 1990 (12), 1147-1148 and Synth. Commun., 1990, 20(22), 3537-3545.

The final step may be a standard reduction step, for example performing a hydrogenation reaction via heterogeneous catalysis in the presence of Pd/C, Pd(II)/C or Raney Ni, or alternatively performing a reduction reaction with a metal, for example zinc, iron, tin, etc. (Advanced Organic Chemistry, 4th edition, 1992, J. MARCH, WILEY Interscience; Reduction in Organic Chemistry, M. Hudlicky, 1983, Ellis Honwood series Chemical Science).

A second synthetic route may be represented schematically as follows:

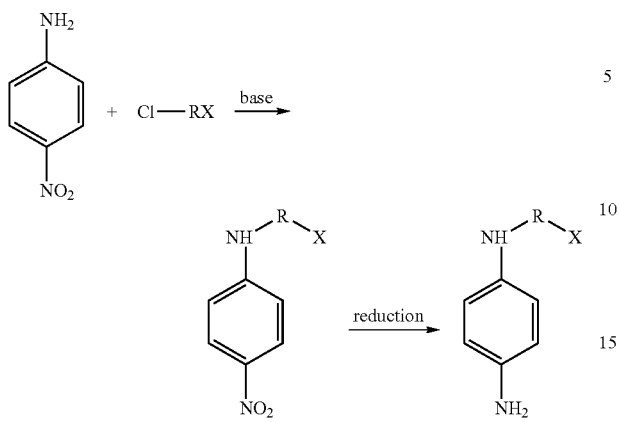

The first synthetic step is described in the scientific reviews J. Indian. Chem. Soc. 1990, 67, 602-603 and Synth. Commun. 1999, 29, 1819-1833.

The second step is a reduction step identical to that described above.

The present disclosure also relates to the nitro compounds of formula (II) and the addition salts thereof:

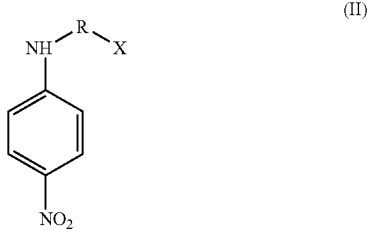

(II)

wherein R and X are as defined above, and with the exclusion of 6-N-(4-nitrophenyl)aminocaproic acid.

Another embodiment of the present disclosure relates to processes for preparing the secondary para-phenylenediamine compounds of formula (I) having a carboxyl group, by reducing a nitro compound corresponding to the paraphenylenediamine of formula (I), i.e., a compound wherein the amino group para to the group —NHR in formula (I) is replaced with a nitro group.

The present disclosure also relates to the use of the compound of formula (I) and the addition salts thereof for the oxidation dyeing of the hair:

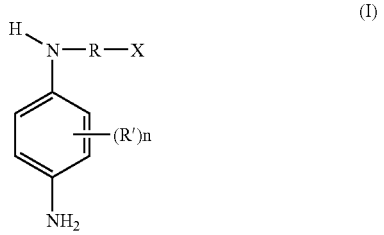

(I)

wherein:

n is an integer ranging from 0 to 4, if n ranges from 1 to 4, then R is a linear or branched $C_1$-$C_{10}$ alkylene radical, which is unsubstituted or substituted with at least one group chosen from hydroxyl, ($C_1$-$C_{15}$)alkylcarbonyl, carboxyl, amido, ($C_1$-$C_{15}$) alkoxycarbonyl, and mono- and di($C_1$-$C_{15}$)alkylaminocarbonyl radicals, wherein the alkylene radical optionally comprises at least one hetero atom chosen from oxygen and nitrogen;

if n is equal to 0, then R is a linear or branched $C_2$-$C_{10}$ alkylene radical, which is unsubstituted or substituted with at least one group chosen from hydroxyl, $C_1$-$C_{15}$ alkoxy, ($C_1$-$C_{15}$)alkylcarbonyl, carboxyl, amido, ($C_1$-$C_{15}$)alkoxycarbonyl, and mono- and di($C_1$-$C_{15}$)alkylaminocarbonyl radicals wherein the alkylene radical optionally comprises at least one hetero atom chosen from oxygen and nitrogen;

X is a radical —COOY, wherein Y is chosen from:
a hydrogen atom;
a $C_1$-$C_{15}$ alkyl radical; and
a $C_1$-$C_{15}$ monohydroxyalkyl or polyhydroxyalkyl radical;

R' is chosen from a $C_1$-$C_{15}$ alkyl radical, a $C_1$-$C_{15}$ alkoxy radical, a $C_1$-$C_{15}$ hydroxyalkoxy radical, a ($C_1$-$C_{15}$) alkoxy($C_1$-$C_{15}$)alkyl radical, a $C_1$-$C_{15}$ monohydroxyalkyl or polyhydroxyalkyl radical, and a chlorine atom;

wherein the compound of formula (I) is not 6-N-(4-aminophenyl)aminocaproic acid.

The present disclosure also relates to a cosmetic composition for dyeing fibers, including keratin fibers such as hair, comprising, in a medium that is suitable for dyeing, at least one compound of formula (I) and the addition salts thereof:

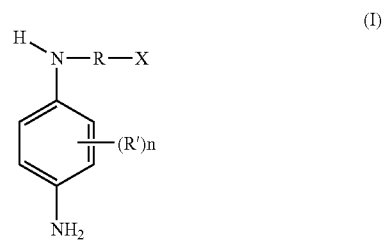

(I)

wherein:

n is an integer ranging from 0 to 4, if n ranges from 1 to 4, then R is a linear or branched $C_1$-$C_{10}$ alkylene radical, which is unsubstituted or substituted with at least one group chosen from hydroxyl, ($C_1$-$C_{15}$)alkylcarbonyl, carboxyl, amido, ($C_1$-$C_{15}$) alkoxycarbonyl, mono($C_1$-$C_{15}$)alkylaminocarbonyl, and di($C_1$-$C_{15}$)alkylaminocarbonyl radicals, wherein the alkylene radical optionally comprises at least one hetero atom chosen from oxygen and nitrogen;

if n is equal to 0, then R is a linear or branched $C_2$-$C_{10}$ alkylene radical, which is unsubstituted or substituted with at least one group chosen from hydroxyl, $C_1$-$C_{15}$ alkoxy, ($C_1$-$C_{15}$)alkylcarbonyl, carboxyl, amido, ($C_1$-$C_{15}$)alkoxycarbonyl, mono($C_1$-$C_{15}$)alkylaminocarbonyl, and di($C_1$-$C_{15}$)alkylaminocarbonyl, radicals wherein the alkylene radical optionally comprises at least one hetero atom chosen from oxygen and nitrogen;

X is a radical —COOY, wherein Y is chosen from:
  a hydrogen atom;
  a $C_1$-$C_{15}$ alkyl radical; and
  a $C_1$-$C_{15}$ monohydroxyalkyl or polyhydroxyalkyl radical;
R' is chosen from a $C_1$-$C_{15}$ alkyl radical, a $C_1$-$C_{15}$ alkoxy radical, a $C_1$-$C_{15}$ hydroxyalkoxy radical, a ($C_1$-$C_{15}$) alkoxy($C_1$-$C_{15}$)alkyl radical, a $C_1$-$C_{15}$ monohydroxyalkyl radical, and a $C_1$-$C_{15}$ polyhydroxyalkyl radical, and a chlorine atom;
wherein the compound of formula (I) is not 6-N-(4-aminophenyl)aminocaproic acid.

In one embodiment of the present disclosure, when n is equal to 0, then the group R of formula (I) is a linear or branched $C_2$-$C_{10}$ alkylene radical, such as ethylene, propylene, butylene, pentylene or hexylene, which is unsubstituted or substituted with at least one group chosen from ($C_2$-$C_8$)alkylcarbonyl, carboxyl and ($C_2$-$C_8$)alkoxycarbonyl radicals, wherein the alkylene radical optionally comprises at least one oxygen atom.

In another embodiment of the present disclosure, when n ranges from 1 to 4, then the group R of formula (I) is a linear or branched $C_2$-$C_{10}$ alkylene radical, such as ethylene, propylene; butylene, pentylene or hexylene, which is unsubstituted or substituted with at least one group chosen from ($C_2$-$C_8$)alkylcarbonyl, carboxyl and ($C_2$-$C_8$)alkoxycarbonyl radicals, wherein the alkylene radical optionally comprises at least one oxygen atom.

In one embodiment of the present disclosure, the group X of formula (I) is a radical —COOY, wherein Y is chosen from a hydrogen atom and a $C_1$-$C_6$ alkyl radical, such as methyl, ethyl, isopropyl or tert-butyl.

In another embodiment, the group R' of formula (I) is chosen from a $C_1$-$C_6$-alkyl radical, such as methyl, ethyl, n-propyl, or isopropyl, a $C_1$-$C_6$ alkoxy radical, a $C_1$-$C_6$ hydroxyalkoxy radical, such as β-hydroxyethoxy, a ($C_1$-$C_6$) alkoxy($C_1$-$C_6$)alkyl radical, and a $C_1$-$C_6$ monohydroxyalkyl or polyhydroxyalkyl radical.

In another embodiment of the present disclosure, the composition contains at least one compound of formula (I) chosen from the following compounds:
  tert-Butyl 3-(4-aminophenylamino)propionate;
  3-[4-Amino-2-(2-hydroxyethoxy)phenylamino]propionic acid;
  Diethyl 2-(4-aminophenylamino)pentanedioate;
  Dimethyl 2-(4-aminophenylamino)succinate;
  Ethyl 3-(4-aminophenylamino)butyrate;
  Ethyl 4-(4-aminophenylamino)butyrate;
  Methyl 6-(4-aminophenylamino)hexanoate;
  Dimethyl 2-(4-aminophenylamino)pentanedioate;
  Methyl 4-(4-aminophenylamino)butyrate;
  di-tert-Butyl 2-(4-aminophenylamino)pentanedioate;
  Ethyl 3-(4-aminophenylamino)propionate;
  Methyl 3-(4-aminophenylamino)propionate;
  6-(4-Amino-2-methylphenylamino)hexanoic acid;
  3-(4-Amino-2-methylphenylamino)propionic acid;
  Diethyl 2-(4-amino-2-methylphenylamino)pentanedioate;
  Dimethyl 2-(4-amino-2-methylphenylamino)succinate;
  Ethyl 3-(4-amino-2-methylphenylamino)butyrate;
  Ethyl 4-(4-amino-2-methylphenylamino)butyrate;
  Methyl 6-(4-amino-2-methylphenylamino)hexanoate;
  Dimethyl 2-(4-amino-2-methylphenylamino)pentanedioate;
  Methyl 4-(4-amino-2-methylphenylamino)butyrate;
  di-tert-Butyl 2-(4-amino-2-methylphenylamino)pentanedioate;
  Ethyl 3-(4-amino-2-methylphenylamino)propionate;
  Methyl 3-(4-amino-2-methylphenylamino)propionate;
  tert-Butyl 3-(4-amino-2-methylphenylamino)propionate;
  Ethyl 2-(4-aminophenylamino)-3-methylbutyrate;
  6-(4-Amino-3-methylphenylamino)hexanoic acid;
  3-(4-Amino-2-methylphenylamino)propionic acid;
  Diethyl 2-(4-amino-3-methylphenylamino)pentanedioate;
  Dimethyl 2-(4-amino-3-methylphenylamino)succinate;
  Ethyl 3-(4-amino-3-methylphenylamino)butyrate;
  Ethyl 4-(4-amino-3-methylphenylamino)butyrate;
  Methyl 6-(4-amino-3-methylphenylamino)hexanoate;
  Dimethyl 2-(4-amino-3-methylphenylamino)pentanedioate;
  Methyl 4-(4-amino-3-methylphenylamino)butyrate;
  di-tert-Butyl 2-(4-amino-3-methylphenylamino)pentanedioate;
  Ethyl 3-(4-amino-3-methylphenylamino)propionate;
  Methyl 3-(4-amino-3-methylphenylamino)propionate;
  tert-Butyl 3-(4-amino-3-methylphenylamino)propionate; and
  tert-Butyl 2-(4-aminophenylamino)propionate.

In one embodiment of the present disclosure, the compound of formula (I) is present in an amount ranging from 0.0001% to 20% by weight, relative to total weight of the composition, such as from 0.005% to 6% by weight relative to the total weight of the composition.

The medium that is suitable for dyeing comprises water or a mixture of water and at least one organic solvent, such as branched or unbranched $C_1$-$C_4$ lower alcohols, such as ethanol and isopropanol; polyols and polyol ethers, such as 2-butoxyethanol, propylene glycol, propylene glycol monomethyl ether, diethylene glycol monomethyl ether and monoethyl ether, glycerol, and also aromatic alcohols, such as benzyl alcohol or phenoxyethanol, and mixtures thereof.

In one embodiment, the solvents can be present in amounts ranging from 1% to 40% by weight, relative to the total weight of the dye composition, such as from 5% to 30% by weight, relative to the total weight of the dye composition.

In another aspect of the present disclosure, the cosmetic composition may comprise at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents or opacifiers, and vitamins or provitamins.

The above adjuvants can each be present in an amount ranging from 0.01% to 20% by weight relative to the weight of the composition.

The composition of the invention may also comprise at least one oxidation coupler.

Among the oxidation couplers that may be used, non-limiting mention may be made of meta-phenylenediamines, meta-aminophenols, meta-diphenols, naphthalene-based couplers and heterocyclic couplers, and also the addition salts thereof.

Non-limiting examples of oxidation couplers that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino- 3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof.

In one embodiment of the present disclosure, the at least one oxidation coupler is present in an amount ranging from 0.0001% to 20% by weight, relative to the total weight of the composition, such as from 0.005% to 6% by weight, relative to the total weight of the composition.

The composition of the present disclosure may contain at least one additional oxidation base other than the compound of formula (I).

In one example of an embodiment of the present disclosure, the additional oxidation bases may be chosen from para-phenylenediamines, bis(phenyl)alkylenediamines, para-aminophenols, ortho-aminophenols and heterocyclic bases, and the addition salts thereof.

Among the para-phenylenediamines that may be used, non-limiting mention may be made, by way of example, of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methyl-aniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine and 6-(4-aminophenylamino)hexan-1-ol, and the acid addition salts thereof.

Among the para-phenylenediamines mentioned above, further non-limiting mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine and the acid addition salts thereof.

Among the bis(phenyl)alkylenediamines that may be used, non-limiting mention may be made, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl) tetramethylenediamine, N,N'-bis(4-methylaminophenyl) tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the acid addition salts thereof.

Among the para-aminophenols that may be used, non-limiting mention may be made, by way of example, of para-aminophenol, 4-amino-3-methylphenol, 4-amino-3-fluorophenol, 4-amino-2-chlorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6 [((5'-amino-2'-hydroxy-3'-methyl)phenyl)methyl]-2-methylphenol and bis(5'-amino-2'-hydroxy)phenylmethane and the acid addition salts thereof.

Among the ortho-aminophenols that may be used, non-limiting mention may be made, by way of example, of 2-aminophenol, 2-amino-5-methylphenol, 2-amino-6-methylphenol and 5-acetamido-2-aminophenol, and the acid addition salts thereof.

Among the heterocyclic bases that may be used, non-limiting mention may be made, by way of example, of pyridine derivatives, pyrimidine derivatives and pyrazole derivatives.

Among the pyridine derivatives that may be used, non-limiting mention may be made of the compounds described, for example, in British Patent Nos. GB 1,026,978 and GB 1,153,196, as well as 2,5-diaminopyridine, 2-(4-methoxyphenyl)amino-3-aminopyridine, and 3,4-diaminopyridine, and the addition salts thereof with an acid.

Other pyridine oxidation bases that can be used in the compositions according to the present disclosure include the 3-aminopyrazolo[1,5-a]pyridine oxidation bases or the addition salts thereof described, for example, in French Patent Application No. FR 2 801 308. Non-limiting examples that may be mentioned include pyrazolo[1,5-a]pyrid-3-ylamine; 2-acetylaminopyrazolo[1,5-a]pyrid-3-ylamine; 2-morpholin-4-ylpyrazolo-[1,5-a]pyrid-3-ylamine; 3-aminopyrazolo[1,5-a]pyridin-2-carboxylic acid; 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyrid-3,7-diamine; 7-morpholin-4-ylpyrazolo-[1,5-a]pyrid-3-ylamine; pyrazolo[1,5-a]pyrid-3,5-diamine; 5-morpholin-4-ylpyrazolo[1,5-a]pyrid-3-ylamine; 2-[(3-aminopyrazolo[1,5-a]pyrid-5-yl)-(2-hydroxyethyl)amino]ethanol; 2-[(3-aminopyrazolo[1,5-a]pyrid-7-yl)-(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol; and also the acid addition salts thereof.

Among the pyrimidine derivatives that may be used, non-limiting mention may be made of the compounds described, for example, in German Patent No. DE 2359399; Japanese Patent Nos. JP 88-169571 and JP 05-63124; European Patent No. EP 0 770 375 or Patent Application No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine and the addition salts thereof and the tautomeric forms thereof, when a tautomeric equilibrium exists.

Among the pyrazole derivatives that may be used, non-limiting mention may be made of the compounds described in German Patent Nos. DE 38 43 892 and DE 41 33 957;

Patent Application Nos. WO 94/08969 and WO 94/08970; French Patent Application No. FR-A-2 733 749; and German Patent Application No. DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof.

In one embodiment of the present disclosure, the at least one additional oxidation base is present in an amount ranging from 0.0001% to 20% by weight, relative to the total weight of the composition, such as from 0.005% to 6% by weight, relative to the total weight of the composition.

In one aspect of the present disclosure, the addition salts that may be used for the oxidation bases and couplers can be chosen from the addition salts with an acid such as the hydrochlorides, hydrobromides, sulfates, citrates, succinates, tartrates, lactates, tosylates, benzenesulfonates, phosphates and acetates, and the salts with a base, such as the addition salts with sodium hydroxide, potassium hydroxide, ammonia, amines or alkanolamines.

The dye composition in accordance with the present disclosure may also contain one or more direct dyes, which may be chosen from neutral, acidic or cationic nitrobenzene dyes, neutral, acidic or cationic azo direct dyes, neutral, acidic or cationic quinone, such as, for example, anthraquinone direct dyes, azine direct dyes, methine direct dyes, azomethine direct dyes, triarylmethane direct dyes, indoamine direct dyes, and natural direct dyes. In a further embodiment of the present disclosure, the composition may comprise at least one direct dye chosen from cationic direct dyes and natural direct dyes.

Among the cationic direct dyes that may be used according to the invention, non-limiting mention may be made of the cationic azo direct dyes described in patent application Nos. WO 95/15144 and WO 95/01772, and European Patent Application No. EP 714 954.

Among these compounds that may be used, non-limiting mention may be made of the following dyes:
  1,3-dimethyl-2-[[4-(dimethylamino)phenyl]azo]-1H-imidazolium chloride;
  1,3-dimethyl-2-[(4-aminophenyl)azo]-1H-imidazolium chloride; and
  1-methyl-4-[(methylphenylhydrazono)methyl]pyridinium methyl sulfate.

Among the natural direct dyes that may be used according to the present disclosure, non-limiting mention may be made of lawsone, juglone, alizarin, purpurin, carminic acid, kermesic acid, purpurogallin, protocatechaldehyde, indigo, isatin, curcumin, spinulosin, and apigenidin. Further non-limiting mention may be made to the use of extracts or decoctions containing these natural dyes and also henna-based poultices or extracts.

The at least one direct dye can be present, for example, in an amount ranging from 0.001% to 20% by weight, relative to the total weight of the composition, such as from 0.005% to 10% by weight, relative to the total weight of the composition.

A person skilled in the art will take care to select the adjuvants, additional oxidation dye precursors, oxidation couplers and direct dyes such that the beneficial properties associated with the dye composition in accordance with the present disclosure are not, or are not substantially, adversely affected by the envisaged addition(s).

A ready-to-use dye composition according to the present disclosure can be obtained by adding one or more oxidizing agents. The oxidizing agents conventionally used for the oxidation dyeing of keratin fibers are chosen from, for example, hydrogen peroxide, urea peroxide, alkali metal bromates, persalts such as perborates and persulfates, peracids and oxidase enzymes, among which non-limiting mention may be made of peroxidases, two-electron oxidoreductases such as uricases, and four-electron oxygenases, for instance laccases. In one embodiment of the present disclosure, hydrogen peroxide is used in the dye composition.

The pH of the dye composition in accordance with the present disclosure can range from 3 and 12, for instance, from 5 to 11. The pH may be adjusted to the desired value using acidifying or basifying agents usually used in the dyeing of keratin fibers, or alternatively using standard buffer systems.

Among the acidifying agents that may be used, non-limiting mention may be made, for example, of mineral or organic acids other than carboxylic diacids, such as hydrochloric acid, orthophosphoric acid, sulfuric acid, carboxylic acids such as acetic acid, tartaric acid, citric acid and lactic acid, and sulfonic acids.

Among the basifying agents that may be used, non-limiting mention may be made, for example, of aqueous ammonia, alkali metal carbonates, alkanolamines such as monoethanolamine, diethanolamine and triethanolamine and also derivatives thereof, sodium hydroxide, potassium hydroxide and the compounds of formula (III):

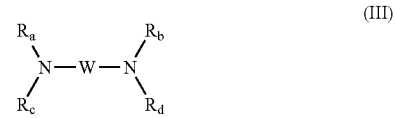

wherein W is a propylene residue optionally substituted with a hydroxyl group or a $C_1$-$C_4$ alkyl radical; $R_a$, $R_b$, $R_c$ and $R_d$, which may be identical or different, are chosen from a hydrogen atom, a $C_1$-$C_4$ alkyl and a $C_1$-$C_4$ hydroxyalkyl radical.

The dye composition according to the present disclosure may be in various forms, such as in the form of liquids, creams or gels, or in any other form that is suitable for dyeing keratin fibers, such as human hair.

Another aspect of the present disclosure relates to a process in which the composition as disclosed herein is applied to the fibers and the color is developed using an oxidizing agent. The color may be developed at acidic, neutral or alkaline pH. The oxidizing agent may be added to the composition of the present disclosure just at the time of use. The oxidizing agent may be used starting with an oxidizing composition containing it, which is applied simultaneously or sequentially to the fibers at the time of application of the dye composition.

According to one embodiment of the composition of the present disclosure, the dye composition is mixed, such as at the time of use, with a composition comprising, in a medium that is suitable for dyeing, at least one oxidizing agent, this oxidizing agent being present in an amount that is sufficient to develop a coloration. The mixture obtained is then applied to the keratin fibers. After an action time of 3 to 50 minutes, such as 5 to 30 minutes, the keratin fibers are rinsed, washed with shampoo, rinsed again and then dried.

The oxidizing composition may contain various adjuvants conventionally used in hair dye compositions and as defined above.

The pH of the oxidizing composition containing the oxidizing agent can be such that, after mixing with the dye composition, the pH of the resulting composition applied to the keratin fibers can range from 3 to 12, for instance, from 5 to 11. It may be adjusted to the desired value by means of acidifying or basifying agents usually used in the dyeing of keratin fibers and as defined above.

The ready-to-use composition that is finally applied to the keratin fibers may be in various forms, such as in the form of liquids, creams or gels, or in any other form that is suitable for dyeing keratin fibers, such as human hair.

The present disclosure also relates to the use of the cosmetic composition according to the disclosure comprising, in a medium that is suitable for dyeing, at least one compound of formula (I) for dyeing fibers, such as keratin fibers including hair.

Another embodiment of the present disclosure comprises a multi-compartment device or dyeing "kit", in which a first compartment contains the dye composition defined above and a second compartment contains an oxidizing composition. This kit may be equipped with an applicator for applying the desired mixture to the hair, such as the devices described in French Patent FR-2 586 913.

Using this device, it is possible to dye keratin fibers via a process that includes mixing a dye composition in accordance with the present disclosure with an oxidizing agent as defined above, and applying the mixture obtained to the keratin fibers for a time that is sufficient to develop the desired coloration.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurement.

The examples that follow serve to illustrate the present disclosure without, however, being limiting in nature.

EXAMPLES

Example 1

Synthesis of 3-[4-amino-2-(2-hydroxyethoxy)phenylamino]propionic acid, dihydrochloride (5)

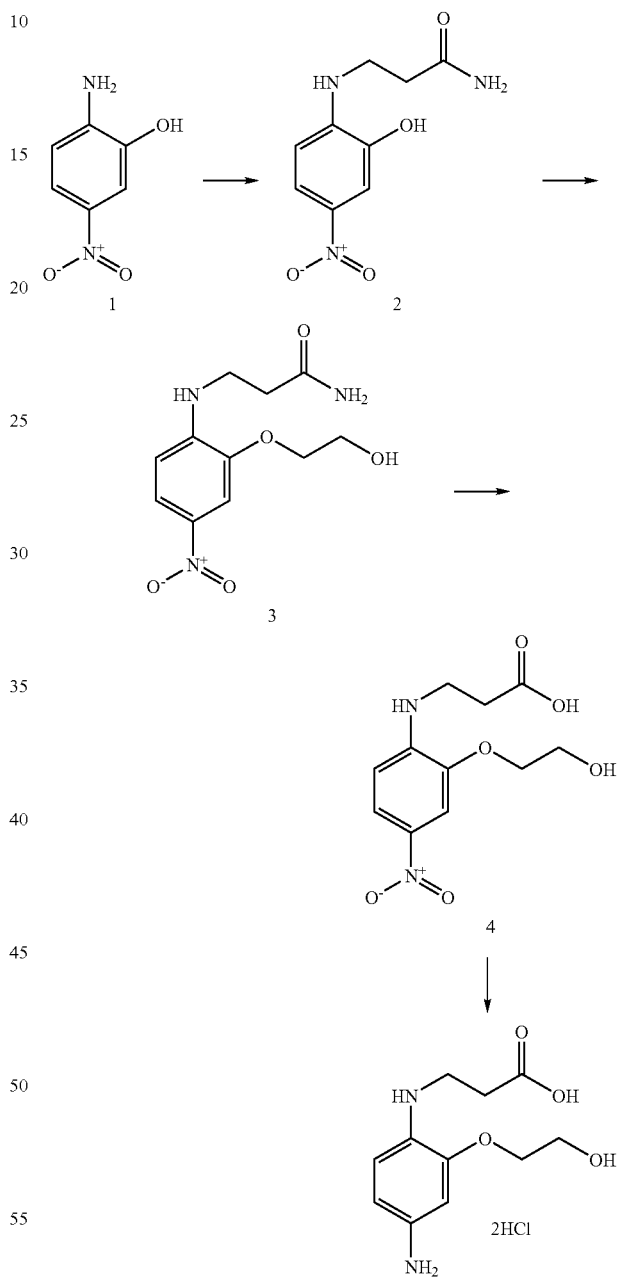

Step 1: Preparation of
3-(2-hydroxy-4-nitrophenylamino)propionamide (2)

15 g (0.1 mol) of 2-amino-5-nitrophenol, 7.8 g (0.11 mol) of acrylamide, 3 drops of 96% sulfuric acid and 20 mg of hydroquinone were maintained at 100° C. for 45 minutes.

The mixture dissolved and an insoluble material was then formed, which was filtered off. This precipitate was taken up in 100 ml of refluxing toluene; after filtering while hot, 18 g of powder were obtained after re-slurrying in hot ethyl acetate (m.p.=194° C.).

|   | theory | found |
|---|--------|-------|
| C | 48.00  | 47.73 |
| H | 4.92   | 5.03  |
| N | 18.66  | 18.57 |

Step 2: Preparation of 3-[2-(2-hydroxyethoxy)-4-nitrophenylamino]propionamide 2 g (8.8 mmol) of 3-(2-hydroxy-4-nitrophenylamino) propionamide obtained above dissolved in 10 ml of dimethylformamide and 7 ml of 15% alcoholic potassium hydroxide (0.015 mol) were brought to 95° C. 14 ml (0.2 mol) of 2-bromoethanol were added to this mixture and, after heating for 2.5 hours, the reaction mixture was poured onto a mixture of ice and water. The yellow precipitate was filtered off by suction, washed with 1 N sodium hydroxide and with water, and then dried. After recrystallization from ethanol, 2.1 g of yellow powder were obtained. m.p.=184° C.

|   | theory | found |
|---|--------|-------|
| C | 49.07  | 48.98 |
| H | 5.62   | 5.91  |
| N | 15.61  | 14.76 |

Step 3: Preparation 3-[2-(2-hydroxyethoxy)-4-nitrophenylamino]propionic acid (4)

1 g of 3-[2-(2-hydroxyethoxy)-4-nitrophenylamino]propionamide (6), heated for 1 hour on a boiling water bath in the presence of 4 ml of hydrochloric acid (d=1.18) and poured into 5 g of ice, gave, after filtering by suction and drying, a yellow powder whose elemental analysis was as follows:

|   | theory | found |
|---|--------|-------|
| C | 48.89  | 48.04 |
| H | 5.22   | 5.85  |
| N | 10.37  | 11.03 |

Step 4: Preparation of 3-[4-amino-2-(2-hydroxyethoxy)phenylamino]propionic acid dihydrochloride (5)

The 3-[2-(2-hydroxyethoxy)-4-nitrophenylamino]propionic acid (7) obtained in the preceding step was reduced in the presence of zinc/$NH_4Cl$ to give the expected 3-[4-amino-2-(2-hydroxyethoxy)phenylamino]propionic acid dihydrochloride.

The proton NMR and mass spectra were in accordance with the expected structure of the product.

Colored locks of hair were obtained after applying a composition obtained by mixing a standard dye support comprising the compound obtained above with an oxidizing composition comprising hydrogen peroxide.

Example 2

Synthesis of ethyl 3-(4-aminophenylamino)propionate dihydrochloride (7)

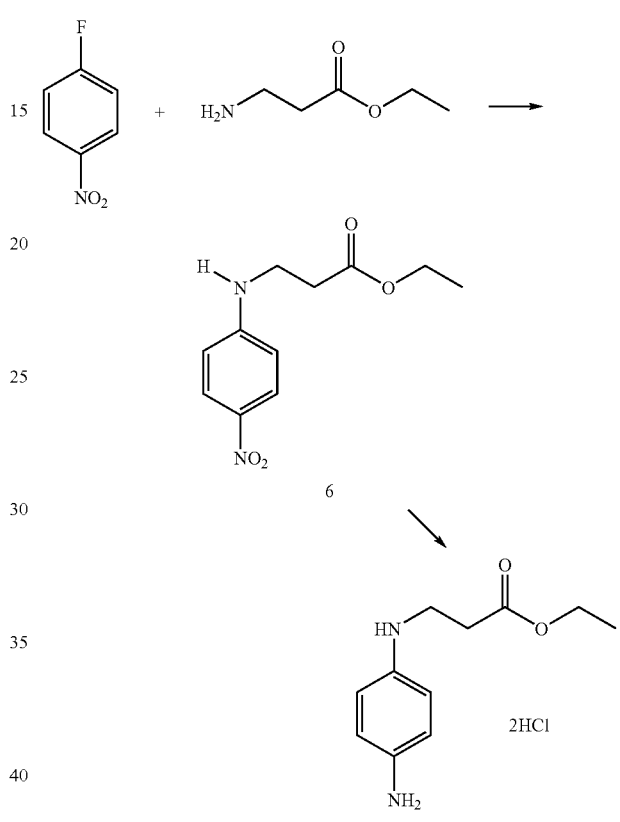

Step 1: Synthesis of ethyl 3-(4-nitrophenylamino)propionate (6)

459 mg of 4-fluoronitrobenzene, 500 mg of β-alanine ethyl ester and 1.15 ml of $Et_3N$ were added to a solution of 10 ml of N-methylpyrrolidinone (NMP). The reaction medium was heated at 70° C. for 8 hours and, after cooling to room temperature, was then poured into a water and ice mixture. The yellow precipitate formed was filtered off, re-slurried in water and then dried over $P_2O_5$. 520 mg of ethyl 3-(4-nitrophenylamino)propionate (6) were obtained.

Step 2: Synthesis of ethyl 3-(4-aminophenylamino)propionate dihydrochloride (7)

The product obtained during the preceding step was reduced with a boiling zinc/ammonium chloride/water/ethanol mixture. The corresponding amine was isolated in dihydrochloride form.

The proton NMR and mass spectra were in accordance with the expected structure of the product.

Colored locks of hair were obtained after applying a composition obtained by mixing a standard dye support comprising the compound obtained above with an oxidizing composition comprising hydrogen peroxide.

Example 3

Synthesis of ethyl 2-(4-aminophenylamino)-3-methylbutyrate dihydrochloride (9)

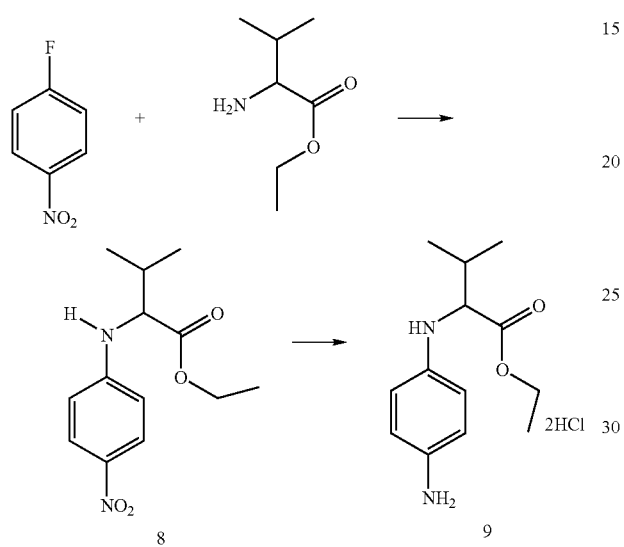

Step 1: Synthesis of ethyl 2-(4-nitrophenylamino)-3-methylbutyrate (8)

162 mg of 4-fluoronitrobenzene, 200 mg of L-valine ethyl ester and 0.4 ml of $Et_3N$ were added to a solution of 10 ml of N-methylpyrrolidinone (NMP). The reaction medium was heated at 70° C. for 8 hours and, after cooling to room temperature, then poured into a water and ice mixture. The yellow precipitate formed was filtered off, re-slurried in water and then dried over $P_2O_5$. 100 mg of ethyl 2-(4-nitrophenylamino)-3-methylbutyrate (8) were obtained.

Step 2: Synthesis of ethyl 2-(4-aminophenylamino)-3-methylbutyrate dihydrochloride (9)

The compound obtained during the preceding step was reduced with a boiling zinc/ammonium chloride/water/ethanol mixture. The corresponding amine was isolated in dihydrochloride form.

The proton NMR and mass spectra were in accordance with the expected structure of the product.

Colored locks of hair were obtained after applying a composition obtained by mixing a standard dye support comprising the compound obtained above with an oxidizing composition comprising hydrogen peroxide.

Example 4

Synthesis of tert-butyl 2-(4-aminophenylamino)propionate dihydrochloride (11)

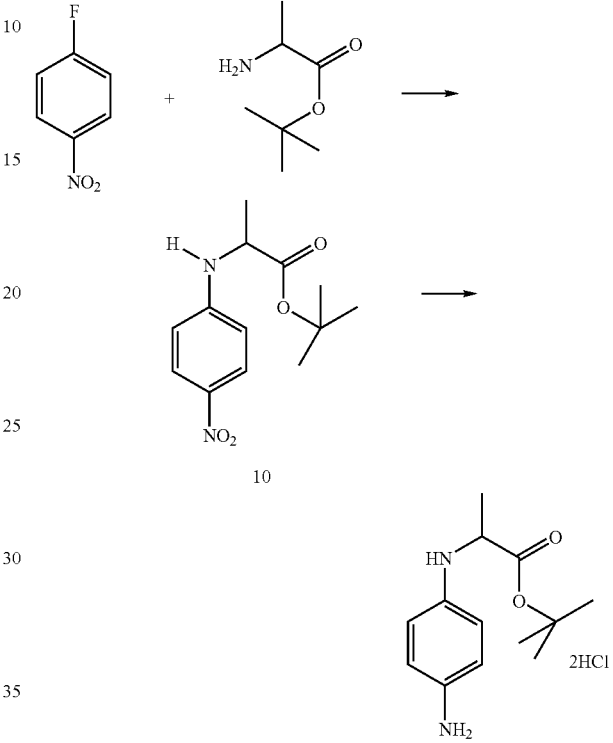

Step 1: Synthesis tert-butyl 2-(4-nitrophenylamino)propionate (10)

388 mg of 4-fluoronitrobenzene, 500 mg of L-alanine tert-butyl ester and 0.9 ml of $Et_3N$ were added to a solution of 10 ml of N-methylpyrrolidinone. The reaction medium was heated at 70° C. for 20 hours and, after cooling to room temperature, then poured into a water and ice mixture. The yellow precipitate formed was filtered off, re-slurried in water and then dried over $P_2O_5$. 246 mg of tert-butyl 2-(4-nitrophenylamino)propionate (10) were obtained.

Step 2: Synthesis of tert-butyl 2-(4-aminophenylamino)propionate dihydrochloride (11)

The compound obtained during the preceding step was reduced with a boiling zinc/ammonium chloride/water/ethanol mixture. The corresponding amine was isolated in dihydrochloride form.

Colored locks of hair were obtained after applying a composition obtained by mixing a standard dye support comprising the compound obtained above with an oxidizing composition comprising hydrogen peroxide.

Example 5

Synthesis of 3-(4-amino-2-methylphenylamino)propionic acid ethyl ester (13)

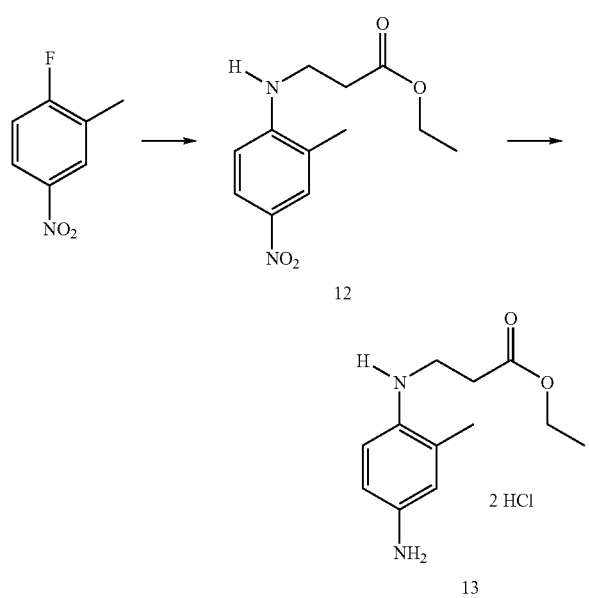

Step 1: Preparation of ethyl 3-[(2-methyl-4-nitrophenylamino]propionate (12)

3.1 g (0.02 mol) of 2-fluoro-5-nitrotoluene, 4.7 g (0.045 mol) of sodium carbonate, 3.8 g (0.022 mol) of ethyl 3-aminopropanoate hydrochloride and 15 ml of N-methylpyrrolidinone were introduced into a three-necked flask under nitrogen. The mixture was heated to 90° C. After reaction for 48 hours, the reaction mixture was cooled and 50 ml of distilled water were then added slowly with vigorous stirring. The nitro derivative appeared in the form of a yellow semi-solid, and was extracted with dichloromethane and then purified on a column of silica, eluting with 2/3 ethyl acetate/heptane. 3.2 g of expected nitro derivative (12) were obtained in the form of a yellow powder.

Step 2: Preparation of 3-(4-amino-2-methylphenylamino)propionic acid ethyl ester (13)

2 g of nitro derivative (12) prepared above and about 50 ml of methanol were introduced into a 200 ml autoclave (hydrogenator) equipped with a mechanical stirrer. The solution obtained was degassed with nitrogen. 0.2 g of palladium-on-charcoal (5% humidity, containing 50% water) was added thereto. The reaction mixture was stirred, while flushing once with hydrogen, and hydrogen was then introduced to a pressure of about 5 bar. After reaction for 6 hours, the reactor was flushed with nitrogen and the reaction mixture was filtered quickly through Celite under a gentle pressure of nitrogen. The filtrate was recovered in a pre-cooled solution of methanol containing 3 equivalents of hydrochloride gas. The filter cake was rinsed several times with methanol under a stream of nitrogen. The solution thus obtained was concentrated and then treated with ether. The product obtained in the form of a pale pink paste was stirred and then rinsed several times with acetonitrile and ether under nitrogen. 2.3 g of expected product (13) were isolated in the form of a slightly pink-white powder.

The proton and $^{13}C$ NMR spectra and microanalyses were in accordance with the expected structure of the product.

Example 6

Synthesis of methyl 6-[(4-amino-3-methylphenyl)amino]hexanoate dihydrochloride (15)

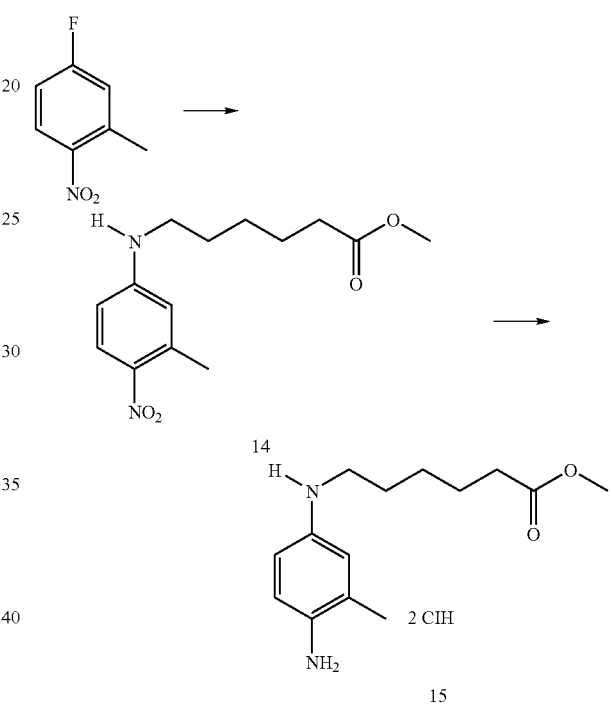

Step 1: Preparation of methyl 6-[(3-methyl-4-nitrophenyl)amino]hexanoate (14)

3.1 g (0.02 mol) of 5-fluoro-2-nitrotoluene, 4.7 g (0.045 mol) of sodium carbonate, 4.5 g (0.025 mol) of methyl-6-aminohexanoate hydrochloride and 20 ml of N-methylpyrrolidinone were introduced into a three-necked flask under nitrogen. The mixture was heated to 90° C. After reaction for 56 hours, the reaction mixture was cooled and 50 ml of distilled water were then added slowly with vigorous stirring. A yellow precipitate appeared. This precipitate was filtered off, washed several times with water and then with pentane, and dried under vacuum. 5.3 g of expected nitro derivative were obtained in the form of a yellow powder.

Step 2: Preparation of methyl 6-[(4-amino-3-methylphenyl)amino]hexanoate dihydrochloride (15)

2.3 g of nitro derivative (14) prepared above and about 100 ml of methanol were introduced into a 200 ml autoclave (hydrogenator) equipped with a magnetic stirrer. The solution obtained was degassed with nitrogen. 0.4 g of palladium-on-charcoal (5% humidity, containing 50% water) was added thereto. The reaction mixture was stirred, while flushing once with hydrogen, and hydrogen was then introduced to a pressure of about 5 bar. After reaction for 4 hours, the reactor was flushed with nitrogen. The reaction mixture was filtered quickly through Celite under a gentle pressure of nitrogen. The filtrate was recovered into a precooled solution of methanol containing about 3 equivalents of hydrogen chloride gas. The filter cake was rinsed several times with methanol under a stream of nitrogen. The solution thus obtained was concentrated and then treated with ether. The product obtained, in the form of a pale pink paste, was stirred and then rinsed several times with acetonitrile and with ether under nitrogen. 2.1 g of expected product (15) were isolated in the form of a slightly pink-white powder.

The proton and $^{13}C$ NMR spectra and microanalyses were in accordance with the expected structure of the product.

Example 7

Synthesis of
3-[(4-aminophenyl)amino]-2-hydroxypropanoic acid
dihydrochloride (16)

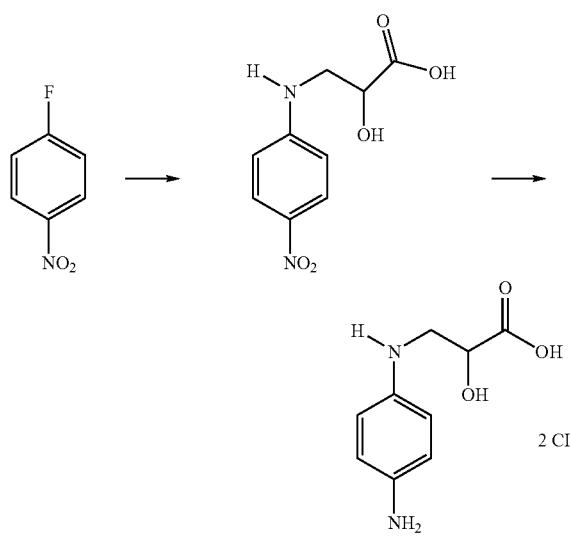

Fluoronitrobenzene (0.2 mmol in 400 µL of N-methyl-pyrrolidinone) and DL-isoserine (0.24 mmol in 500 µL of N-methyl-pyrrolidinone) were heated at 80° C. for 24 hours in the presence of potassium carbonate (0.2 mmol in 500 µL of water). The reaction medium was then cooled and concentrated under vacuum. The residue was taken up in 2 mL of ethanol and cyclohexene (1 mL) was added, along with a suspension of 50 mg of 5% palladium-on-charcoal in 500 µL of ethanol. This mixture was heated at 80° C. for 3 hours. The reaction medium was then filtered and treated with a hydrochloric ethanol solution. The solution was then concentrated to give the expected derivative in dihydrochloride form.

The proton and $^{13}C$ NMR spectra and microanalyses were in accordance with the expected structure of the product.

Example 8

Synthesis of
4-[(4-aminophenyl)amino]-3-hydroxybutanoic acid
hydrochloride (17)

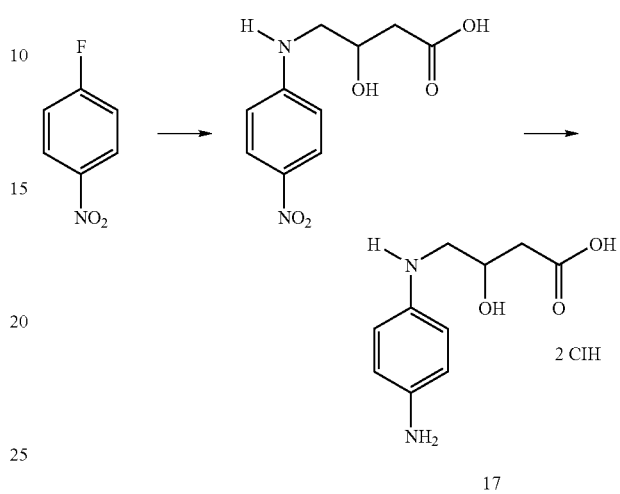

Fluoronitrobenzene (0.2 mmol in 400 µL of N-methyl-pyrrolidinone) and DL-4-amino-3-hydroxybutyric acid (0.24 mmol in 500 µL of N-methyl-pyrrolidinone) were heated at 80° C. for 24 hours in the presence of potassium carbonate (0.2 mmol in 500 µL of water). The reaction medium was then cooled and concentrated under vacuum. The residue was taken up in 2 mL of ethanol, and cyclohexene (1 mL) was added, along with a suspension of 50 mg of 5% palladium-on-charcoal in 500 µL of ethanol. This mixture was heated at 80° C. for 3 hours. The reaction medium was then filtered and treated with a hydrochloric ethanol solution. The solution was then concentrated to give the expected derivative in dihydrochloride form.

The proton and $^{13}C$ NMR spectra and microanalyses were in accordance with the expected structure of the product.

What is claimed is:

1. A secondary para-phenylenediamine compound chosen from:
   tert-Butyl 3-(4-aminophenylamino)propionate;
   3-[4-Amino-2-(2-hydroxyethoxy)phenylamino]propionic acid;
   Diethyl 2-(4-aminophenylamino)pentanedioate;
   Dimethyl 2-(4-aminophenylamino)succinate;
   Ethyl 3-(4-aminophenylamino)butyrate;
   Ethyl 4-(4-aminophenylamino)butyrate;
   Methyl 6-(4-aminophenylamino)hexanoate;
   Dimethyl 2-(4-aminophenylamino)pentanedioate;
   Methyl 4-(4-aminophenylamino)butyrate;
   di-tert-Butyl 2-(4-aminophenylamino)pentanedioate;
   Ethyl 3-(4-aminophenylamino)propionate;
   Methyl 3-(4-aminophenylamino)propionate;
   6-(4-Amino-2-methylphenylamino)hexanoic acid;
   3-(4-Amino-2-methylphenylamino)propionic acid;
   Diethyl 2-(4-amino-2-methylphenylamino)pentanedioate;
   Dimethyl 2-(4-amino-2-methylphenylamino)succinate;
   Ethyl 3-(4-amino-2-methylphenylamino)butyrate;
   Ethyl 4-(4-amino-2-methylphenylamino)butyrate;
   Methyl 6-(4-amino-2-methylphenylamino)hexanoate;

Dimethyl 2-(4-amino-2-methylphenylamino)pentanedioate;
Methyl 4-(4-amino-2-methylphenylamino)butyrate;
di-tert-Butyl 2-(4-amino-2-methylphenylamino)pentanedioate;
Ethyl 3-(4-amino-2-methylphenylamino)propionate;
Methyl 3-(4-amino-2-methylphenylamino)propionate;
tert-Butyl 3-(4-amino-2-methylphenylamino)propionate;
Ethyl 2-(4-aminophenylamino)-3-methylbutyrate;
6-(4-Amino-3-methylphenylamino)hexanoic acid;
Diethyl 2-(4-amino-3-methylphenylamino)pentanedioate;
Dimethyl 2-(4-amino-3-methylphenylamino)succinate;
Ethyl 3-(4-amino-3-methylphenylamino)butyrate;
Ethyl 4-(4-amino-3-methylphenylamino)butyrate;
Methyl 6-(4-amino-3-methylphenylamino)hexanoate;
Dimethyl 2-(4-amino-3-methylphenylamino)pentanedioate;
Methyl 4-(4-amino-3-methylphenylamino)butyrate;
di-tert-Butyl 2-(4-amino-3-methylphenylamino)pentanedioate;
Ethyl 3-(4-amino-3-methylphenylamino)propionate;
Methyl 3-(4-amino-3-methylphenylamino)propionate;
tert-Butyl 3-(4-amino-3-methylphenylamino)propionate;
tert-Butyl 2-(4-aminophenylamino)propionate; and
the addition salts thereof.

2. The compound according to claim 1, wherein the addition salts of said compound are acid addition salts chosen from hydrochlorides, hydrobromides, sulfates, citrates, succinates, tartrates, lactates, tosylates, benzenesulfonates, phosphates, and acetates.

3. A composition for dyeing keratin fibers, comprising, in a medium that is suitable for dyeing, at least one secondary para-phenylenediamine compound of formula (I) and the addition salts thereof:

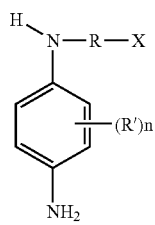

(I)

wherein:

n is an integer ranging from 1 to 4,

R is a linear or branched $C_2$-$C_{10}$ alkylene radical, which is unsubstituted or substituted with at least one group chosen from hydroxyl, $(C_1$-$C_{15})$alkylcarbonyl, carboxyl, amido, $(C_1$-$C_{15})$alkoxycarbonyl, mono$(C_1$-$C_{15})$alkylamino-carbonyl, and di$(C_1$-$C_{15})$alkylaminocarbonyl radicals, wherein the alkylene radical optionally comprises at least one hetero atom chosen from oxygen and nitrogen;

X is a radical —COOY, wherein Y is chosen from:
 a hydrogen atom;
 a $C_1$-$C_{15}$ alkyl radical; and
 a $C_1$-$C_{15}$ monohydroxyalkyl or polyhydroxyalkyl radical;

R' is chosen from a $C_1$-$C_{15}$ alkyl radical, a $C_1$-$C_{15}$ alkoxy radical, a $C_1$-$C_{15}$ hydroxyalkoxy radical, a $(C_1$-$C_{15})$ alkoxy$(C_1$-$C_{15})$alkyl radical, a $C_1$-$C_{15}$ monohydroxyalkyl radical, and a $C_1$-$C_{15}$ polyhydroxyalkyl radical, and a chlorine atom.

4. The composition according to claim 3, wherein R is a linear or branched $C_2$-$C_{10}$ alkylene radical, which is unsubstituted or substituted with at least one group chosen from $(C_2$-$C_8)$alkylcarbonyl, carboxyl, and $(C_2$-$C_8)$alkoxycarbonyl radicals, and said alkylene radical optionally comprises at least one oxygen atom.

5. The composition according to claim 3, wherein X is a radical —COOY, wherein Y is chosen from a hydrogen atom and a $C_1$-$C_6$ alkyl radical.

6. The composition according to claim 3, wherein R' is chosen from a $C_1$-$C_6$ alkyl radical, a $C_1$-$C_6$ alkoxy radical, a $C_1$-$C_6$ hydroxyalkoxy radical, a $(C_1$-$C_6)$alkoxy-$(C_1$-$C_6)$ alkyl radical, a $C_1$-$C_6$ monohydroxyalkyl radical, and a $C_1$-$C_6$ polyhydroxyalkyl radical.

7. The composition according to claim 3 wherein the at least one secondary para-phenylenediamine compound is present in an amount ranging from 0.0001% to 20% by weight relative to the total weight of the composition.

8. The composition according to claim 7, wherein the at least one secondary para-phenylenediammine compound is present in an amount ranging from 0.005% to 6% by weight relative to the total weight of the composition.

9. The composition according claim 3, wherein the medium that is suitable for dyeing comprises water or a mixture of water and at least one organic solvent chosen from branched or unbranched $C_1$-$C_4$ lower alcohols; polyols and polyol ethers; aromatic alcohols; and mixtures thereof.

10. The composition according to claim 3, wherein the composition further comprises at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents or opacifiers, and vitamins or provitamins.

11. The composition according to claim 10, wherein each cosmetic adjuvant is present in an amount ranging from 0.01% to 20% by weight relative to the total weight of the composition.

12. The composition according to claim 3, wherein the composition further comprises at least one oxidation coupler chosen from meta-phenylenediamines, meta-aminophenols, meta-diphenols, naphthalene-based couplers, and heterocyclic couplers, and the addition salts thereof.

13. The composition according to claim 12, wherein the at least one oxidation coupler is present in an amount ranging from 0.0001% to 20% by weight relative to the total weight of the composition.

14. The composition according to claim 3,
 further comprising at least one oxidation base chosen from bis(phenyl)alkylenediamines, para-aminophenols, ortho-aminophenols, heterocyclic bases, and the addition salts thereof, and para-phenylenediamines other than the secondary para-phenylenediamine compounds of formula (I) and
 the addition salts thereof.

15. The composition according to claim 14, wherein the at least one oxidation base is present in an amount ranging from 0.0001% to 20% by weight relative to the total weight of the composition.

16. The composition according to claim 3, further comprising at least one natural or cationic direct dye.

17. A process for oxidation dyeing of keratin fibers, comprising:

applying a dye composition to the fibers for a time sufficient to develop a desired coloration, in the presence of an oxidizing agent, wherein the dye composition comprises, in a medium that is suitable for dyeing keratin fibers, at least one secondary paraphenylenediamine compound chosen from:
tert-Butyl 3-(4-aminophenylamino)propionate;
3-[4-Amino-2-(2-hydroxyethoxy)phenylamino]propionic acid;
Diethyl 2-(4-aminophenylamino)pentanedioate;
Dimethyl 2-(4-aminophenylamino)succinate;
Ethyl 3-(4-aminophenylamino)butyrate;
Ethyl 4-(4-aminophenylamino)butyrate;
Methyl 6-(4-aminophenylamino)hexanoate;
Dimethyl 2-(4-aminophenylamino)pentanedioate;
Methyl 4-(4-aminophenylamino)butyrate;
di-tert-Butyl 2-(4-aminophenylamino)pentanedioate;
Ethyl 3-(4-aminophenylamino)propionate;
Methyl 3-(4-aminophenylamino)propionate;
6-(4-Amino-2-methylphenylamino)hexanoic acid;
3-(4-Amino-2-methylphenylamino)propionic acid;
Diethyl 2-(4-amino-2-methylphenylamino)pentanedioate;
Dimethyl 2-(4-amino-2-methylphenylamino)succinate;
Ethyl 3-(4-amino-2-methylphenylamino)butyrate;
Ethyl 4-(4-amino-2-methylphenylamino)butyrate;
Methyl 6-(4-amino-2-methylphenylamino)hexanoate;
Dimethyl 2-(4-amino-2-methylphenylamino)pentanedioate;
Methyl 4-(4-amino-2-methylphenylamino)butyrate;
di-tert-Butyl 2-(4-amino-2-methylphenylamino)pentanedioate;
Ethyl 3-(4-amino-2-methylphenylamino)propionate;
Methyl 3-(4-amino-2-methylphenylamino)propionate;
tert-Butyl 3-(4-amino-2-methylphenylamino)propionate;
Ethyl 2-(4-aminophenylamino)-3-methylbutyrate;
6-(4-Amino-3-methylphenylamino)hexanoic acid;
Diethyl 2-(4-amino-3-methylphenylamino)pentanedioate;
Dimethyl 2-(4-amino-3-methylphenylamino)succinate;
Ethyl 3-(4-amino-3-methylphenylamino)butyrate;
Ethyl 4-(4-amino-3-methylphenylamino)butyrate;
Methyl 6-(4-amino-3-methylphenylamino)hexanoate;
Dimethyl 2-(4-amino-3-methylphenylamino)pentanedioate;
Methyl 4-(4-amino-3-methylphenylamino)butyrate;
di-tert-Butyl 2-(4-amino-3-methylphenylamino)pentanedioate;
Ethyl 3-(4-amino-3-methylphenylamino)propionate;
Methyl 3-(4-amino-3-methylphenylamino)propionate;
tert-Butyl 3-(4-amino-3-methylphenylamino)propionate;
tert-Butyl 2-(4-aminophenylamino)propionate; and
the addition salts thereof.

18. A ready-to-use composition, comprising:
a dye composition comprising at least one secondary para-phenylenediamine compound
chosen from:
tert-Butyl 3-(4-aminophenylamino)propionate;
3-[4-Amino-2-(2-hydroxyethoxy)phenylamino]propionic acid;
Diethyl 2-(4-aminophenylamino)pentanedioate;
Dimethyl 2-(4-aminophenylamino)succinate;
Ethyl 3-(4-aminophenylamino)butyrate;
Ethyl 4-(4-aminophenylamino)butyrate;
Methyl 6-(4-aminophenylamino)hexanoate;
Dimethyl 2-(4-aminophenylamino)pentanedioate;
Methyl 4-(4-aminophenylamino)butyrate;
di-tert-Butyl 2-(4-aminophenylamino)pentanedioate;
Ethyl 3-(4-aminophenylamino)propionate;
Methyl 3-(4-aminophenylamino)propionate;
6-(4-Amino-2-methylphenylamino)hexanoic acid;
3-(4-Amino-2-methylphenylamino)propionic acid;
Diethyl 2-(4-amino-2-methylphenylamino)pentanedioate;
Dimethyl 2-(4-amino-2-methylphenylamino)succinate;
Ethyl 3-(4-amino-2-methylphenylamino)butyrate;
Ethyl 4-(4-amino-2-methylphenylamino)butyrate;
Methyl 6-(4-amino-2-methylphenylamino)hexanoate;
Dimethyl 2-(4-amino-2-methylphenylamino)pentanedioate;
Methyl 4-(4-amino-2-methylphenylamino)butyrate;
di-tert-Butyl 2-(4-amino-2-methylphenylamino)pentanedioate;
Ethyl 3-(4-amino-2-methylphenylamino)propionate;
Methyl 3-(4-amino-2-methylphenylamino)propionate;
tert-Butyl 3-(4-amino-2-methylphenylamino)propionate;
Ethyl 2-(4-aminophenylamino)-3-methylbutyrate;
6-(4-Amino-3-methylphenylamino)hexanoic acid;
Diethyl 2-(4-amino-3-methylphenylamino)pentanedioate;
Dimethyl 2-(4-amino-3-methylphenylamino)succinate;
Ethyl 3-(4-amino-3-methylphenylamino)butyrate;
Ethyl 4-(4-amino-3-methylphenylamino)butyrate;
Methyl 6-(4-amino-3-methylphenylamino)hexanoate;
Dimethyl 2-(4-amino-3-methylphenylamino)pentanedioate;
Methyl 4-(4-amino-3-methylphenylamino)butyrate;
di-tert-Butyl 2-(4-amino-3-methylphenylamino)pentanedioate;
Ethyl 3-(4-amino-3-methylphenylamino)propionate;
Methyl 3-(4-amino-3-methylphenylamino)propionate;
tert-Butyl 3-(4-amino-3-methylphenylamino)propionate;
tert-Butyl 2-(4-aminophenylamino)propionate; and
the addition salts thereof; and
at least one oxidizing agent chosen from hydrogen peroxide, urea peroxide, alkali metal bromates, persalts, peracids and oxidase enzymes.

19. A multi-compartment kit for dyeing keratin fibers comprising
a first compartment comprising a dye composition, comprising, in a medium suitable for dyeing keratin fibers, at least one compound
chosen from:
tert-Butyl 3-(4-aminophenylamino)propionate;
3-[4-Amino-2-(2-hydroxyethoxy)phenylamino]propionic acid;
Diethyl 2-(4-aminophenylamino)pentanedioate;
Dimethyl 2-(4-aminophenylamino)succinate;
Ethyl 3-(4-aminophenylamino)butyrate;
Ethyl 4-(4-aminophenylamino)butyrate;
Methyl 6-(4-aminophenylamino)hexanoate;
Dimethyl 2-(4-aminophenylamino)pentanedioate;
Methyl 4-(4-aminophenylamino)butyrate;
di-tert-Butyl 2-(4-aminophenylamino)pentanedioate;
Ethyl 3-(4-aminophenylamino)propionate;
Methyl 3-(4-aminophenylamino)propionate;
6-(4-Amino-2-methylphenylamino)hexanoic acid;
Diethyl 2-(4-amino-2-methylphenylamino)pentanedioate;
Dimethyl 2-(4-amino-2-methylphenylamino)succinate;
Ethyl 3-(4-amino-2-methylphenylamino)butyrate;
Ethyl 4-(4-amino-2-methylphenylamino)butyrate;
Methyl 6-(4-amino-2-methylphenylamino)hexanoate;

Dimethyl 2-(4-amino-2-methylphenylamino)pentanedioate;
Methyl 4-(4-amino-2-methylphenylamino)butyrate;
di-tert-Butyl 2-(4-amino-2-methylphenylamino)pentanediate;
Ethyl 3-(4-amino-2-methylphenylamino)propionate;
Methyl 3-(4-amino-2-methylphenylamino)propionate;
tert-Butyl 3-(4-amino-2-methylphenylamino)propionate;
Ethyl 2-(4-aminophenylamino)-3-methylbutyrate;
6-(4-Amino-3-methylphenylamino)hexanoic acid;
3-(4-Amino-2-methylphenylamino)propionic acid;
Diethyl 2-(4-amino-3-methylphenylamino)pentanedioate;
Dimethyl 2-(4-amino-3-methylphenylamino)succinate;
Ethyl 3-(4-amino-3-methylphenylamino)butyrate;
Ethyl 4-(4-amino-3-methylphenylamino)butyrate;
Methyl 6-(4-amino-3-methylphenylamino)hexanoate;
Dimethyl 2-(4-amino-3-methylphenylamino)pentanedioate;
Methyl 4-(4-amino-3-methylphenylamino)butyrate;
di-tert-Butyl 2-(4-amino-3-methylphenylamino)pentanedoate;
Ethyl 3-(4-amino-3-methylphenylamino)propionate;
Methyl 3-(4-amino-3-methylphenylamino)propionate;
tert-Butyl 3-(4-amino-3-methylphenylamino)propionate;
tert-Butyl 2-(4-aminophenylamino)propionate;
the addition salts thereof; and
a second compartment comprising an oxidizing agent.

20. A composition for dyeing keratin fibers, comprising, in a medium that is suitable for dyeing, at least one secondary para-phenylenediamine compound chosen from:
tert-Butyl 3-(4-aminophenylamino)propionate;
3-[4-Amino-2-(2-hydroxyethoxy)phenylamino]propionic acid;
Diethyl 2-(4-aminophenylamino)pentanedioate;
Dimethyl 2-(4-aminophenylamino)succinate;
Ethyl 3-(4-aminophenylamino)butyrate;
Ethyl 4-(4-aminophenylamino)butyrate;
Methyl 6-(4-aminophenylamino)hexanoate;
Dimethyl 2-(4-aminophenylamino)pentanedioate;
Methyl 4-(4-aminophenylamino)butyrate;
di-tert-Butyl 2-(4-aminophenylamino)pentanedioate;
Ethyl 3-(4-aminophenylamino)propionate;
Methyl 3-(4-aminophenylamino)propionate;
6-(4-Amino-2-methylphenylamino)hexanoic acid;
3-(4-Amino-2-methylphenylamino)propionic acid;
Diethyl 2-(4-amino-2-methylphenylamino)pentanedioate;
Dimethyl 2-(4-amino-2-methylphenylamino)succinate;
Ethyl 3-(4-amino-2-methylphenylamino)butyrate;
Ethyl 4-(4-amino-2-methylphenylamino)butyrate;
Methyl 6-(4-amino-2-methylphenylamino)hexanoate;
Dimethyl 2-(4-amino-2-methylphenylamino)pentanedioate;
Methyl 4-(4-amino-2-methylphenylamino)butyrate;
di-tert-Butyl 2-(4-amino-2-methylphenylamino)pentanedioate;
Ethyl 3-(4-amino-2-methylphenylamino)propionate;
Methyl 3-(4-amino-2-methylphenylamino)propionate;
tert-Butyl 3-(4-amino-2-methylphenylamino)propionate;
Ethyl 2-(4-aminophenylamino)-3-methylbutyrate;
6-(4-Amino-3-methylphenylamino)hexanoic acid;
Diethyl 2-(4-amino-3-methylphenylamino)pentanedioate;
Dimethyl 2-(4-amino-3-methylphenylamino)succinate;
Ethyl 3-(4-amino-3-methylphenylamino)butyrate;
Ethyl 4-(4-amino-3-methylphenylamino)butyrate;
Methyl 6-(4-amino-3-methylphenylamino)hexanoate;
Dimethyl 2-(4-amino-3-methylphenylamino)pentanedioate;
Methyl 4-(4-amino-3-methylphenylamino)butyrate;
di-tert-Butyl 2-(4-amino-3-methylphenylamino)pentanedioate;
Ethyl 3-(4-amino-3-methylphenylamino)propionate;
Methyl 3-(4-amino-3-methylphenylamino)propionate;
tert-Butyl 3-(4-amino-3-methylphenylamino)propionate;
tert-Butyl 2-(4-aminophenylamino)propionate; and the addition salts thereof.

21. The composition of claim 20 wherein the at least one para-phenylenediamine compound is present in an amount ranging from 0.0001% to 20% by weight relative to the total weight of the composition.

22. The composition of claim 21, wherein the at least one para-phenylenediamine compound is present in an amount ranging from 0.005% to 6% by weight relative to the total weight of the composition.

23. The composition of claim 20, wherein the medium that is suitable for dyeing comprises water or a mixture of water and at least one organic solvent chosen from branched or unbranched $C_1$-$C_4$ lower alcohols; polyols and polyol ethers; aromatic alcohols; and mixtures thereof.

24. The composition of claim 20, further comprising at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents or opacifiers, and vitamins or provitamins.

25. The composition of claim 24, wherein each cosmetic adjuvant is present in an amount ranging from 0.01% to 20% by weight relative to the total weight of the composition.

26. The composition of claim 20, further comprising at least one oxidation coupler chosen from meta-phenylenediamines, meta-aminophenols, meta-diphenols, naphthalene-based couplers, and heterocyclic couplers, and the addition salts thereof.

27. The composition of claim 26, wherein the at least one oxidation coupler is present in an amount ranging from 0.0001% to 20% by weight relative to the total weight of the composition.

28. The composition of claim 20, further comprising at least one oxidation base chosen from bis(phenyl)alkylenediamines, para-aminophenols, ortho-aminophenols, heterocyclic bases, and the addition salts thereof, and para-phenylenediamines other than the secondary para-phenylenediamine compounds recited in claim 20, and the addition salts thereof.

29. The composition of claim 28, wherein the at least one oxidation base is present in an amount ranging from 0.0001% to 20% by weight relative to the total weight of the composition.

30. The composition of claim 20, further comprising at least one natural or cationic direct dye.

* * * * *

UNITED STATES PATENT AND TRADEMARK OFFICE
CERTIFICATE OF CORRECTION

PATENT NO. : 7,384,432 B2 Page 1 of 1
APPLICATION NO. : 11/066450
DATED : June 10, 2008
INVENTOR(S) : Stéphane Sabelle et al.

It is certified that error appears in the above-identified patent and that said Letters Patent is hereby corrected as shown below:

In claim 9, column 36, line 26, "according claim" should read --according to claim--.

Signed and Sealed this

Eighteenth Day of November, 2008

JON W. DUDAS
*Director of the United States Patent and Trademark Office*